(12) United States Patent
Huang et al.

(10) Patent No.: US 9,102,717 B2
(45) Date of Patent: Aug. 11, 2015

(54) ANTIBODY SPECIFIC FOR APOLIPOPROTEIN AND METHODS OF USE THEREOF

(75) Inventors: Yadong Huang, San Francisco, CA (US); Qin Xu, Albany, CA (US); Thu Nga Bien-Ly, Daly City, CA (US); Karl H. Weisgraber, Walnut Creek, CA (US); Ligong Chen, Fremont, CA (US); Clare Peters-Libeu, Sebastopol, CA (US)

(73) Assignee: THE J. DAVID GLADSTONE INSTITUTES, San Francisco, CA (US)

( * ) Notice: Subject to any disclaimer, the term of this patent is extended or adjusted under 35 U.S.C. 154(b) by 282 days.

(21) Appl. No.: 13/581,785

(22) PCT Filed: Feb. 25, 2011

(86) PCT No.: PCT/US2011/026296
§ 371 (c)(1),
(2), (4) Date: Oct. 2, 2012

(87) PCT Pub. No.: WO2011/109246
PCT Pub. Date: Sep. 9, 2011

(65) Prior Publication Data
US 2013/0017251 A1    Jan. 17, 2013

Related U.S. Application Data

(60) Provisional application No. 61/309,280, filed on Mar. 1, 2010.

(51) Int. Cl.
| *C07K 16/00* | (2006.01) |
| *C12P 21/08* | (2006.01) |
| *A61K 39/395* | (2006.01) |
| *A61K 39/00* | (2006.01) |
| *C07K 16/18* | (2006.01) |

(52) U.S. Cl.
CPC ............. *C07K 16/18* (2013.01); *C07K 2317/34* (2013.01); *C07K 2317/76* (2013.01)

(58) Field of Classification Search
CPC ............... C07K 16/18; C07K 2317/34; C07K 2317/76; C07K 2319/00; C07K 2317/622; C07K 2317/565; C07K 2316/95; C07K 2316/96; C07K 2317/56; C07K 2317/92; C07K 2317/21; C07K 2317/33; C07K 14/47; C07K 16/00; A61K 2039/505; A61K 39/395; A61K 38/00; A61K 2039/6056; A61K 39/00; A61K 39/0005; A61K 39/0007; G01N 2800/2821; G01N 33/6896
See application file for complete search history.

(56) References Cited

U.S. PATENT DOCUMENTS

| 5,670,477 | A | 9/1997 | Poduslo et al. | |
| 6,252,050 | B1 * | 6/2001 | Ashkenazi et al. | 530/387.3 |
| 7,256,273 | B2 | 8/2007 | Basi et al. | |
| 7,612,179 | B2 | 11/2009 | Nordstedt et al. | |
| 7,625,560 | B2 | 12/2009 | Basi et al. | |
| 7,682,795 | B2 * | 3/2010 | Huang | 435/7.1 |
| 7,771,967 | B2 * | 8/2010 | Huang et al. | 435/69.1 |
| 7,964,598 | B2 * | 6/2011 | Mahley et al. | 514/238.8 |
| 8,512,958 | B2 * | 8/2013 | Huang et al. | 435/6.16 |
| 2002/0147999 | A1 | 10/2002 | Huang et al. | |
| 2007/0104715 | A1 * | 5/2007 | Nordstedt et al. | 424/146.1 |
| 2008/0154022 | A1 | 6/2008 | Wu et al. | |
| 2009/0017041 | A1 | 1/2009 | Pfeifer et al. | |
| 2009/0082271 | A1 * | 3/2009 | Mahley et al. | 514/12 |
| 2009/0175853 | A1 | 7/2009 | Frangione et al. | |
| 2009/0175923 | A1 | 7/2009 | Shafer et al. | |
| 2009/0238821 | A1 | 9/2009 | Holtzman et al. | |

FOREIGN PATENT DOCUMENTS

WO    WO 2009/052439    4/2009

OTHER PUBLICATIONS

Weisgraber, et al. "Human Apolipoprotein E. Determination of the Heparin Binding Sites of Apolipoprotein E3", Journal of Biological Chemistry, 1986, vol. 261, No. 5, pp. 2068-2076.

Yamada, et al., "Brief Communication: Immunotargeting of Apolipoprotein E in Amyloid: An Initial Trial in Mice", Annals of Clinical & Laboratory Science, 2009, vol. 39, No. 2, pp. 134-137.

* cited by examiner

*Primary Examiner* — Chang-Yu Wang
(74) *Attorney, Agent, or Firm* — Bozicevic, Field & Francis LLP; Paula A. Borden

(57) ABSTRACT

The present disclosure provides synthetic antibodies specific for an epitope present on an apolipoprotein E polypeptide. The antibodies are useful in various treatment, diagnostic, and monitoring applications, which are also provided.

20 Claims, 13 Drawing Sheets

3H1 heavy chain variable region amino acid sequence

EVQLVESGGGLVKPGGSLKLSCAASGFTFSSYAMSWVRQTPEKRLEWVATISSGGSYTYYPDSVKGRFTISRDNAKNTLYLQMSSLRSEDTAMYYC
ARQFYYGGSYDYFDYWGQGTTLTVS (SEQ ID NO:1)

FIG. 7A

3H1 heavy chain variable region-encoding nucleotide sequence

GAGGTGCAGCTGGTGGAGTCTGGGGGAGGCTTAGTGAAGCCTGGAGGGTCCCTGAAACTCTCCTGTGCAGCCTCTGGATTCACTTTCAGTAG
CTATGCCATGTCTTGGGTTCGCCAGACTCCGGAGAAGAGGCTGGAGTGGGTCGCAACCATTAGTAGTGGTGGTAGTTACACCTACTATCCAG
ACAGTGTGAAGGGGCGATTCACCATCTCCAGAGACAATGCCAAGAACACCCTGTACCTGCAAATGAGCAGTCTGAGGTCTGAGGACACGGCC
ATGTATTACTGTGCAAGACAATTTTATTACTACGGTGGTAGCTACGACTACTTTGACTACTGGGGCCAAGGGACCACGCTCACCGTCTCG
(SEQ ID NO:9)

FIG. 7B

3H1 heavy chain variable region

```
gaggtgcagctggtggagtctgggggaggcttagtgaagcctgagggtcc
 E  V  Q  L  V  E  S  G  G  G  L  V  K  P  G  G  S
ctgaaactctcctgtgcagcctctggattcactttcagtagctatgccatgtcttgggtt
 L  K  L  S  C  A  A  S  G  F  T  F  S  S  Y  A  M  S  W  V
cgccagactccggagaagaggctggagtgggtcgcaaccattagtagtggtggtagttac
 R  Q  T  P  E  K  R  L  E  W  V  A  T  I  S  S  G  G  S  Y
acctactatccagacagtgtgaaggggcgattcaccatctccagagacaatgccaagaac
 T  Y  Y  P  D  S  V  K  G  R  F  T  I  S  R  D  N  A  K  N
accctgtacctgcaaatgagcagtctgaggtctgaggacacggccatgtattactgtgca
 T  L  Y  L  Q  M  S  S  L  R  S  E  D  T  A  M  Y  Y  C  A
agacaatttattactacggtggtagctacgactacttttgactactgggccaagggacc
 R  Q  F  Y  Y  G  G  S  Y  D  Y  F  D  Y  W  G  Q  G  T
acgctcaccgtctcg
 T  L  T  V  S
```

FIG. 7C

3H1 light chain variable region amino acid sequence

DIVLTQSPATLSVTPGDSVSLACRASQSISNNLHWYQQKSHESPRLLIKYAYQSISGIPSRFSGSGSGTDFTLSINSVETEDFGMYFCQQSNSWPLTFGV
GTKLEIKR (SEQ ID NO:5)

FIG. 8A

3H1 light chain variable region-encoding nucleotide sequence

GACATTGTGCTGACCCAGTCTCCAGCCACCCTGTCTGTGACTCCAGGAGATAGCGTCAGTCTTGCCTGCAGGGCCAGCAAAGTATTAGCAAC
AACCTACACTGGTATCAACAAAATCACATGAGTCTCCAAGGCTTCTCATCAAATATGCTTACCAGTCCATCTCTGGATCCCCTCCAGGTTC
AGTGGCAGTGGATCAGGGACAGATTTCACTCTCAGTATCAACAGTGTGGAGACTGAAGATTTTGGAATGTATTTCTGTCAACAGAGTAACAG
CTGGCCTCACGTTCGGTGTGGGACCAAGCTGGAAATAAAACGT (SEQ ID NO:10)

FIG. 8B

3H1 light chain variable region

```
gacattgtgctgacccagtctccagccaccctgtctgtgactccaggagatagcgtcagt
 D  I  V  L  T  Q  S  P  A  T  L  S  V  T  P  G  D  S  V  S
cttgcctgcagggccagcaaagtattagcaacaacctacactggtatcaacaaaaatca
 L  A  C  R  A  S  Q  S  I  S  N  N  L  H  W  Y  Q  Q  K  S
catgagtctccaaggcttctcatcaaatatgcttaccagtccatctctggatcccctcc
 H  E  S  P  R  L  L  I  K  Y  A  Y  Q  S  I  S  G  I  P  S
aggttcagtggcagtggatcagggacagatttcactctcagtatcaacagtgtggagact
 R  F  S  G  S  G  S  G  T  D  F  T  L  S  I  N  S  V  E  T
gaagattttggaatgtatttctgtcaacagagtaacagctggcctctcacgttcggtgtg
 E  D  F  G  M  Y  F  C  Q  Q  S  N  S  W  P  L  T  F  G  V
gggaccaagctgaaataaaacgt
 G  T  K  L  E  I  K  R
```

FIG. 8C

```
E4                                           KVEQAVETEPEPELRQQTEWQSGQRWELALGR  32
E3  MKVLWAALLVTFLAGCQAKVEQAVETEPEPELRQQTEWQSGQRWELALGR  50

E4  FWDYLRWVQTLSEQVQEELLSSQVTQELRALMDETMKELKAYKSELEEQL   82
E3  FWDYLRWVQTLSEQVQEELLSSQVTQELRALMDETMKELKAYKSELEEQL  100

E4  TPVAEETRARLSKELQAAQARLGADMEDVRGRLVQYRGEVQAMLGQSTEE  132
E3  TPVAEETRARLSKELQAAQARLGADMEDVCGRLVQYRGEVQAMLGQSTEE  150

E4  LRVRLASHLRKLRKRLLRDADDLQKRLAVYQAGAREGAERGLSAIRERLG  182
E3  LRVRLASHLRKLRKRLLRDADDLQKRLAVYQAGAREGAERGLSAIRERLG  200

210           220           230
                        .             .             .
E4  PLVEQGRVRAATVGSLAGQPLQERAQAWGERLRARMEEMGSRTRDRLDEV  232
E3  PLVEQGRVRAATVGSLAGQPLQERAQAWGERLRARMEEMGSRTRDRLDEV  250

240           250           260           270           280
              .             .             .             .             .
E4  KEQVAEVRAKLEEQAQQIRLQAEAFQARLKSWFEPLVEDMQRQWAGLVEK  282
E3  KEQVAEVRAKLEEQAQQIRLQAEAFQARLKSWFEPLVEDMQRQWAGLVEK  300

E4  VQAAVGTSAAPVPSDNH  299
E3  VQAAVGTSAAPVPSDNH  317
```

FIG. 9

***Homo sapiens* Aβ₁₋₄₂**

1 daefrhdsgy evhhqklvff aedvgsnkga iiglmvggvv iat

FIG. 10

ANTIBODY SPECIFIC FOR APOLIPOPROTEIN AND METHODS OF USE THEREOF

CROSS-REFERENCE

This application claims the benefit of U.S. Provisional Patent Application No. 61/309,280, filed Mar. 1, 2010, which application is incorporated herein by reference in its entirety.

BACKGROUND

Human apolipoprotein (apo) E, a 34-kDa protein with 299 amino acids, has three major isoforms, apoE2, apoE3, and apoE4. ApoE4 is a major risk factor for Alzheimer's disease (AD). The apoE4 allele, which is found in 65%-80% of cases of sporadic and familial AD, increases the occurrence and lowers the age of onset of the disease.v ApoE has two structural domains—an amino-terminal domain (amino acids (aa) 1-191) containing the receptor binding region (amino acids 135-150) and a carboxyl-terminal domain (amino acids 222-299) containing the lipid binding region (amino acids 241-272), which are linked by a structurally flexible hinge region (amino acids 192-221). Neurotoxic Aβ peptides associated with AD bind to the lipid-binding domain of apoE, stimulating Aβ fibrillization in vitro and Aβ deposition in vivo in an isoform-dependent manner (apoE4>apoE3). ApoE4 correlates with a greater number of plaques in late-onset AD cases.

ApoE can be proteolytically cleaved at its C-terminus to generate neurotoxic fragments in neurons. The primary cleavage sites are Leu-268 and Met-272, which are located in the lipid binding domain of apoE. Due to a conformational difference, apoE4 is much more susceptible than apoE3 to the cleavage, leading to more neurotoxic fragments generated from apoE4 than from apoE3. The neurotoxic apoE fragments are found in human AD brains and can cause tau pathology and mitochondrial impairment, leading to AD-like neuronal and behavioral deficits in transgenic mice.

LITERATURE

U.S. Patent Publication No. 2009/0238821; U.S. Patent Publication No. 2009/0175923; U.S. Patent Publication No. 2009/0175853; U.S. Patent Publication No. 2009/0017041; WO 2009/052439; U.S. Pat. No. 7,612,179; Yamada et al. (2009) *Ann. Clin. Lab. Sci.* 39:134; Weisgraber et al. (1986) *J. Biol. Chem.* 261:2068

SUMMARY OF THE INVENTION

The present disclosure provides synthetic antibodies specific for an epitope present on an apolipoprotein E polypeptide. The antibodies are useful in various treatment, diagnostic, and monitoring applications, which are also provided.

BRIEF DESCRIPTION OF THE DRAWINGS

FIGS. 7A-C provide: an amino acid sequence of the 3H1 antibody heavy chain variable region, where complementarity determining regions (CDRs) are underlined (FIG. 7A); a nucleotide sequence encoding the 3H1 antibody heavy variable region (FIG. 7B); and the translation of the nucleotide sequence of 7B (FIG. 7C).

FIGS. 8A-C provide: an amino acid sequence of the 3H1 antibody light chain variable region, where CDRs are underlined (FIG. 8A); a nucleotide sequence encoding the 3H1 antibody light variable region (FIG. 8B); and the translation of the nucleotide sequence of 8B (FIG. 8C).

FIG. 9 provide amino acid sequences of an apoE4 polypeptide (SEQ ID NO:11) and an apoE3 polypeptide (SEQ ID NO:12).

FIG. 10 provides an amino acid sequence of an Aβ peptide (SEQ ID NO:13).

Definitions

Figure 1:
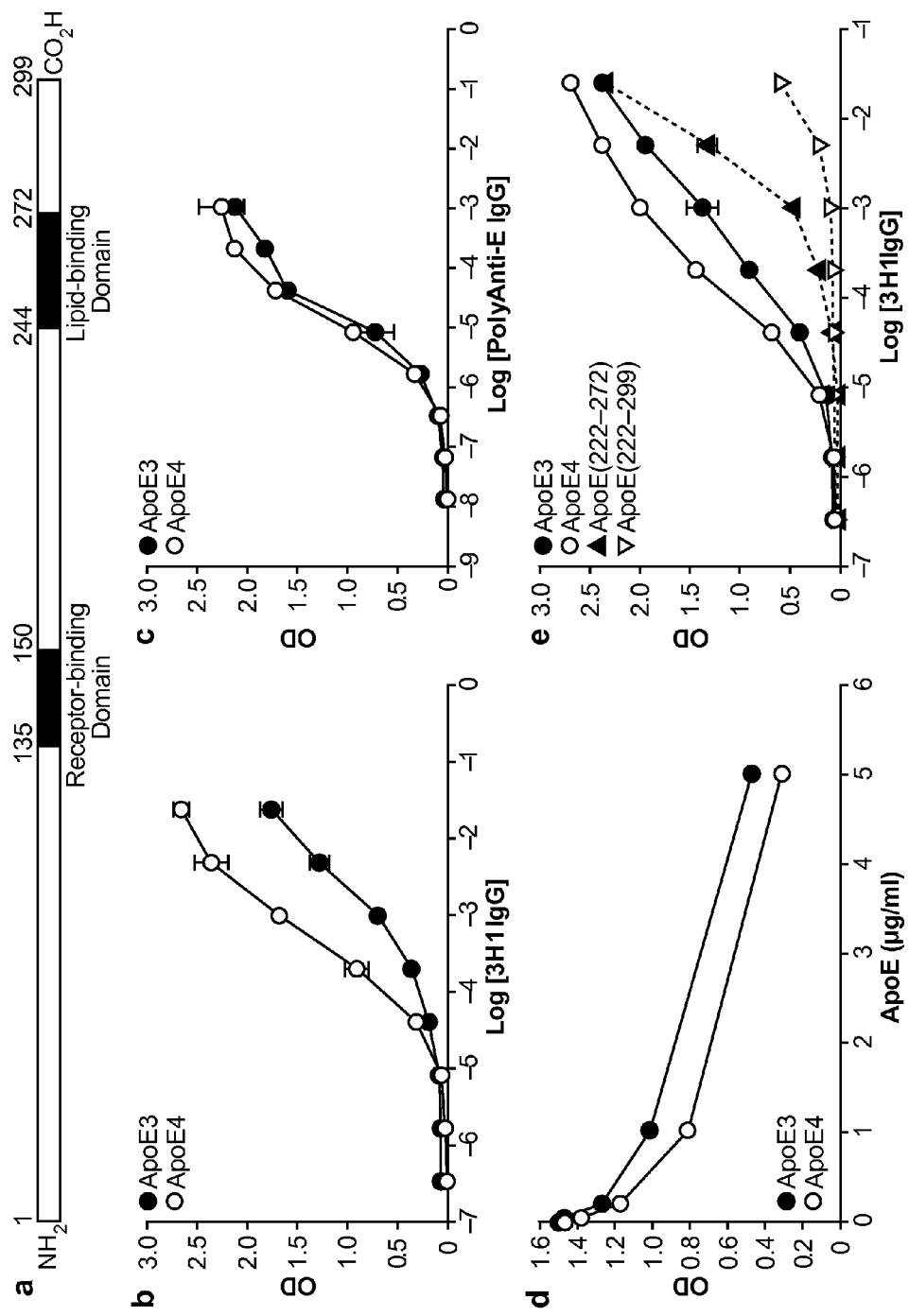
FIGS. 1A-E depict differential reactivity of 3H1 with apoE3 and apoE4.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a compound or a number of cells that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

The terms "polynucleotide" and "nucleic acid" are used interchangeably herein to refer to polymeric forms of nucleotides of any length. The polynucleotides may contain deoxyribonucleotides, ribonucleotides, and/or their analogs.

As used herein, an "apoE4-associated disorder" is any disorder that is caused by the presence of apoE4 in a cell, in the serum, in the interstitial fluid, in the cerebrospinal fluid, or in any other bodily fluid of an individual; any physiological process or metabolic event that is influenced by apoE4 domain interaction; any disorder that is characterized by the presence of apoE4; a symptom of a disorder that is caused by the presence of apoE4 in a cell or in a bodily fluid; a phenomenon associated with a disorder caused by the presence in a cell or in a bodily fluid of apoE4; and the sequelae of any disorder that is caused by the presence of apoE4. ApoE4-associated disorders include apoE4-associated neurological disorders and disorders related to high serum lipid levels. ApoE4-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE4-associated neurological disorders include, but are not limited to, neurofibrillary tangles; amyloid deposits; memory loss; and a reduction in cognitive function. ApoE4-related disorders associated with high serum lipid levels include, but are not limited to, atherosclerosis, and coronary artery disease. Phenomena associated with such apoE4-associated disorders include high serum cholesterol levels.

The term "Alzheimer's disease" (abbreviated herein as "AD") as used herein refers to a condition associated with formation of neuritic plaques comprising amyloid β protein primarily in the hippocampus and cerebral cortex, as well as impairment in both learning and memory. "AD" as used herein is meant to encompass both AD as well as AD-type pathologies.

The term "phenomenon associated with Alzheimer's disease" as used herein refers to a structural, molecular, or functional event associated with AD, including such an event that is readily assessable in an animal model. Such events include, but are not limited to, amyloid deposition, neuropathological developments, learning and memory deficits, and other AD-associated characteristics.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the apolipoprotein epitope" includes reference to one or more apolipoprotein epitopes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides synthetic antibodies specific for an epitope present on an apolipoprotein E polypeptide. The antibodies are useful in various treatment, diagnostic, and monitoring applications, which are also provided.

Antibodies

A subject antibody specifically binds an epitope in apolipoprotein E (apoE), where the epitope comprises amino acid residues within amino acids 222-230 and 261-272 of apoE. Thus, the epitope comprises non-contiguous amino acids.

The epitope recognized by a subject antibody is an epitope comprising non-contiguous amino acids of apoE, e.g., residues within amino acids 222-230 and 261-272 of apoE. For simplicity, this epitope is referred to herein as the "non-contiguous apoE4 epitope." For example, a non-contiguous (conformational) epitope recognized by a subject antibody can comprise an N-terminal portion comprising 3, 4, 5, 6, 7, 8, or 9 contiguous amino acids of the amino acid sequence GSRTRDRLD (SEQ ID NO:14); and a C-terminal portion comprising 3, 4, 5, 6, 7, 8, 9, 10, or 11 contiguous amino acids of the amino acid sequence KSWFEPLVEDM (SEQ ID NO:15). As an example, a non-contiguous (conformational) epitope recognized by a subject antibody can comprise SRTRDRL (SEQ ID NO:16) and SWFEPLVED (SEQ ID NO:17). As another example, a non-contiguous (conformational) epitope recognized by a subject antibody can comprise amino acids GSRTRDRLD (SEQ ID NO:14) and KSWFEPLVEDM (SEQ ID NO:15). The non-contiguous apoE4 epitope can have a length of from about 10 amino acids (aa) to about 15 amino acids (e.g., 10 aa, 11 aa, 12 aa, 13 aa, 14 aa or 15 aa), or from about 15 amino acids to about 25 amino acids (e.g., 15 aa, 16 aa, 17 aa, 18 aa, 19 aa, 20 aa, 21 aa, 22 aa, 23 aa, 24 aa, or 25 aa).

In some embodiments, the non-contiguous apoE epitope comprises an N-terminal portion comprising 8, 9, 10, or 11 contiguous amino acids of the amino acid sequence GSRTRDRLDEV (SEQ ID NO:18); and a C-terminal portion comprising 9, 10, 11, or 12 contiguous amino acids of the amino acid sequence LKSWFEPLVEDM (SEQ ID NO:19). The non-contiguous epitope can have a length of from about 17 aa to about 25 aa, e.g., 17 aa, 18 aa, 19 aa, 20 aa, 21 aa, 22 aa, 23 aa, 24 aa, or 25 aa.

In some embodiments, the epitope recognized by a subject antibody includes a stretch of 20 amino acids to 40 amino acids between the N-terminal portion and the C-terminal portion of the non-contiguous apoE epitope. Thus, for example, the epitope recognized by a subject antibody can include an intervening peptide comprising a stretch of from about 20 amino acids to about 25 amino acids, from about 25 amino acids to 28 amino acids, from 28 amino acids to 30 amino acids, from about 30 amino acids to about 35 amino acids, or from about 35 amino acids to about 40 amino acids. The intervening peptide can comprise an amino acid sequence having at least about 75%, at least about 80%, at least about 85%, at least about 90%, at least about 95%, at least about 98%, at least about 99%, or 100%, sequence identity to a contiguous stretch of 20 aa to 25 aa, or 25 aa to 28 aa, of the following amino acid sequence: KEQVAEVRAKLEEQAQQIRLQAEAFQAR (SEQ ID NO:20). In some embodiments, the intervening peptide has the amino acid sequence: KEQVAEVRAKLEEQAQQIRLQAEAFQAR (SEQ ID NO:20).

In some embodiments, the non-contiguous epitope can be formed by a polypeptide having at least about 75%, at least about 80%, at least about 85%, at least about 90%, at least about 95%, at least about 98%, at least about 99%, or 100%, amino acid sequence identity to a contiguous stretch of 40 aa, 41 aa, 42 aa, 43 aa, 44 aa, 45 aa, 46 aa, 47 aa, 48 aa, 49 aa, 50 aa, or 51 aa, of the sequence: GSRTRDRLDEVKEQVAEVRAKLEEQAQQIRLQAEAFQARLKSWFEPLVEDM(SEQ ID NO:21), where the bold and underlined text indicates amino acids that can form the non-contiguous apoE epitope.

A subject antibody exhibits high affinity binding to apolipoprotein E4 (apoE4). For example, a subject antibody binds to the non-contiguous apoE4 epitope present on an apoE4 polypeptide with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject antibody binds to the non-contiguous apoE epitope present on an apoE4 polypeptide with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

A subject antibody exhibits higher affinity binding to apoE4 than to apolipoprotein E3 (apoE3) in the absence of lipid. Binding of a subject antibody to an apoE3 polypeptide in the absence of lipid is of substantially lower affinity than the specific binding of the antibody to the non-contiguous apoE epitope present on an apoE4 polypeptide. A substantially lower affinity is generally at least a two fold, three fold, five fold, 10 fold, 50 fold, 100 fold, 500 fold, or 1000 fold lower affinity.

A subject antibody exhibits substantially no binding to any epitopes formed by amino acids within amino acids 1-220, or within amino acids 1-210, or within amino acids 1-200, of apoE4. Any binding of a subject antibody to an epitope formed by amino acids within amino acids 1-220, or within amino acids 1-210, or within amino acids 1-200, of apoE4 is generally non-specific binding of a substantially lower affinity than the specific binding of the antibody to the non-contiguous apoE epitope present on an apoE4 polypeptide. A substantially lower affinity is generally at least a two fold, three fold, five fold, 10 fold, 50 fold, 100 fold, 500 fold, or 1000 fold lower affinity.

The non-contiguous apoE epitope recognized by a subject antibody is within the lipid-binding domain of apoE4. Binding of a subject antibody to apoE4 (e.g., binding to the non-contiguous apoE epitope present in an apoE4 polypeptide) is modified by lipid binding. For example, binding affinity of a subject antibody to apoE4 is increased by from about 10% to about 25%, from about 25% to about 50%, from about 50% to about 75%, from about 75% to about 100% (or 2-fold), from about 2-fold to about 5-fold, from about 5-fold to about 10-fold, from about 10-fold to about 25-fold, from about 25-fold to about 50-fold, or greater than 50-fold, in the presence of lipid to which apoE4 binds. Lipids to which apoE4 binds include dimyristoylphosphatidylcholine (DMPC), phosphatidylcholine, dipalmitoylphosphatidylcholine (DPPC), and the like.

Binding of a subject antibody to apoE3 is also increased in the presence of lipid (e.g., DMPC and the like). As noted above, the binding affinity of a subject antibody to apoE3 in the absence of lipid is substantially lower than the binding affinity of a subject antibody to apoE4 in the absence of lipid. In the presence of a lipid such as DMPC, the binding affinity of a subject antibody for apoE3 is increased by from about 10% to about 25%, from about 25% to about 50%, from about 50% to about 75%, from about 75% to about 100% (or 2-fold), from about 2-fold to about 5-fold, from about 5-fold to about 10-fold, from about 10-fold to about 25-fold, from about 25-fold to about 50-fold, or greater than 50-fold, compared to the binding affinity of the antibody for apoE3 in the absence of the lipid.

In some embodiments, a subject antibody binds to apoE present in the Golgi apparatus, but not to apoE present in the endoplasmic reticulum (ER), of a cell such as a neuron or an astrocyte. In some embodiments, a subject antibody binds to apoE present in the Golgi apparatus, but not to apoE present in any other subcellular compartment or to apoE present in the cytoplasm of a cell (e.g., a eukaryotic cell such as a neuron or an astrocyte).

A subject antibody can bind to the core of an amyloid plaque, and the binding substantially co-localizes with amyloid-beta peptide (Aβ) immunoreactivity. For example, a subject antibody can bind, in vitro and/or in vivo, to the non-contiguous apoE epitope present in an apoE4 polypeptide, where the apoE4 polypeptide is present in an amyloid plaque, e.g., a human amyloid plaque. An amyloid plaque can be present in the brain of an individual having Alzheimer's disease (AD). An amyloid plaque can be obtained from the brain of an individual having AD. Whether a subject antibody binds to an amyloid plaque (e.g., a human amyloid plaque), can be determined using any known method, including a method as described in the Examples. Suitable methods include an immunohistochemical method, where the subject antibody being tested is detectably labeled, either directly or indirectly.

The term "human amyloid plaque," as used herein, refers to any amyloid deposits comprising at least one protein having an amino acid sequence encoded by a human gene. A human amyloid plaque can be present in or derived from human tissue. A human amyloid plaque can be present in a sample that has been obtained from a human subject. The human subject can have an amyloid disorder, such as systemic amyloidosis or Alzheimer's disease. The sample can be taken from any tissue or organ containing amyloid plaques. Suitable tissues and organs include brain, tongue, intestines, skeletal muscle, smooth muscle, nerves, skin, ligaments, heart, liver, spleen and kidneys. Where the subject has Alzheimer's disease, the sample is generally a brain section. The brain section is typically obtained post-mortem. Fibrils prepared from any such sample are also included within the term "human amyloid plaques."

The human amyloid plaque can be present in or derived form a non-human animal which is transgenic for one or more, for example two or three, human proteins, which human protein(s) is/are found in amyloid deposits. The human protein can include apoE4, and can also include amyloid precursor protein (APP) (e.g., APP comprising the Swedish mutation), and/or presenilin.

A subject antibody can reduce apoE4-Aβ binding. For example, a subject antibody can reduce apoE4-Aβ binding by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of binding between apoE4 and Aβ in the absence of the antibody.

Aβ includes a polypeptide having a length of from about 35 amino acids to about 50 amino acids, e.g., having a length of from about 35 aa to about 42 aa, from about 42 aa to about 45 aa, or from about 45 aa to about 50 aa; and having at least about 75%, least about 80%, 85%, least about 90%, least about 95%, least about 98%, least about 99%, or 100%, amino acid sequence identity to a contiguous stretch of at least 30 aa, at least 35 aa, at least 40 aa, or 42 aa, of the amino acid sequence depicted in FIG. 10.

A subject antibody can reduce carboxyl-terminal cleavage of apoE4, e.g., by a neuronal cell enzyme that cleaves apoE4 to generate neurotoxic C-terminal apoE4 fragments. A neuronal cell enzyme that cleaves apoE4 to generate neurotoxic C-terminal apoE4 fragments is referred to herein as an apolipoprotein E cleavage enzyme (AECE). A subject antibody can reduce C-terminal cleavage of apoE4 by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of cleavage of apoE4 by the AECE in the absence of the antibody.

A subject antibody can reduce production of neurotoxic C-terminal apoE4 fragments by an AECE in a neuron. For example, a subject antibody can reduce the amount of neurotoxic C-terminal apoE4 fragments produced by action of an AECE in a neuron by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the amount of neurotoxic C-terminal apoE4 fragments produced in the neuron in the absence of the antibody.

The term "apoE cleavage enzyme" ("AECE"), as used herein, is an enzyme that cleaves apoE, e.g., apoE4, to yield neurotoxic apoE fragments. An AECE is a serine protease. In some embodiments, an AECE is present in a mature neuron at higher levels than in an immature neuron. For example, an AECE is present in a mature neuron at a level that is about 25%, about 50%, about 2-fold, about 5-fold, about 10-fold, or more than 10-fold higher than the level in an immature neuron. In some embodiments, an AECE is present in cortical and hippocampal neurons at higher levels than in cerebellar neurons. For example, an AECE is present in cortical and hippocampal neurons at a level that is about 25%, about 50%, about 2-fold, about 5-fold, about 10-fold, or more than 10-fold higher than the level in cerebellar neurons. In some embodiments, an AECE is present in neurons at much higher levels than in astrocytes. For example, an AECE is present in mature neurons at a level that is about 2-fold, about 5-fold, about 10-fold, about 25-fold, about 50-fold, or about 100-fold, or greater than 100-fold, higher than the level in an astrocyte.

Neurotoxic apoE4 fragments that are generated by action of an AECE include carboxyl-terminal truncated apoE4, e.g., carboxyl-terminal truncated apoE4 that include at least amino acids 244-260 of apoE4. Neurotoxic apoE4 fragments include carboxyl-terminal truncated apoE4 that binds both p-tau and p-NF-H. Deletion of from about 28 to about 30, from about 30 to about 35, from about 35 to about 40, from about 40 to about 45, or from about 45 to about 48 amino acids from the carboxyl terminus of apoE3 or apoE4 results in carboxyl-terminal truncated apoE that bind p-tau, bind p-NF-H. Specific neurotoxic carboxyl-terminal truncated apoE4 polypeptides that give rise to neurofibrillary tangles include, but are not limited to, apoE4Δ272-299; apoE3Δ272-299; apoE4Δ261-299; and apoE4Δ252-299. See, e.g., U.S. Pat. No. 6,787,519 for a description of neurotoxic apoE fragments.

Human apolipoprotein (apo) E, a 34-kDa protein with 299 amino acids, has three major isoforms, apoE2, apoE3, and apoE4. Amino acid sequences of apoE polypeptides of various mammalian species are known in the art. See, e.g., Rall et al. (1982) *J. Biol. Chem.* 257:4171; Weisgraber (1994) *Adv. Protein Chem.* 45:249-302; GenBank NP_000032.

An "apoE4 polypeptide" can comprises an amino acid sequence having at least about 75%, at least about 80%, at least about 90%, at least about 95%, at least about 98%, at least about 99%, or 100%, amino acid sequence identity to a contiguous stretch of from about 200 amino acids (aa) to about 225 aa, from about 225 aa to about 250 aa, from about 250 aa to about 275 aa, or from about 275 aa to about 299 aa, of amino acids 19-317 of the apoE4 amino acid sequence depicted in FIG. 9 (SEQ ID NO:11).

An "apoE3 polypeptide" can comprises an amino acid sequence having at least about 75%, at least about 80%, at least about 90%, at least about 95%, at least about 98%, at least about 99%, or 100%, amino acid sequence identity to a contiguous stretch of from about 200 amino acids (aa) to about 225 aa, from about 225 aa to about 250 aa, from about 250 aa to about 275 aa, or from about 275 aa to about 299 aa, of amino acids 19-317 of the apoE3 amino acid sequence depicted in FIG. 9 (SEQ ID NO:12).

The term "antibody" refers to a protein comprising one or two heavy chain variable regions (VH) and/or one or two light chain variable regions (VL), or subfragments thereof capable of binding an epitope. The VH and VL regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) Sequences of Proteins of Immunological Interest, Fifth Edition, U.S. Department of Health and Human Services, NIH Publication No. 91-3242; Chothia et al. (1987) J. Mol. Biol. 196: 901-917). A VH can comprise three CDRs and four FRs arranged from N-terminus to C-terminus in the following order: FR1, CDR1, FR2, CDR2, FR3, CDR3, FR4. Similarly, a VL can comprise three CDRs and four FRs arranged from N-terminus to C-terminus in the following order: FR1, CDR1, FR2, CDR2, FR3, CDR3, FR4.

The VH or VL chain of an antibody can further include all or part of a heavy or light chain constant region, to thereby form a heavy or light immunoglobulin chain, respectively. In one embodiment, the antibody is a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes intact immunoglobulins of types IgA, IgG, IgE, IgD, IgM and subtypes thereof. In some embodiments, a subject antibody is an IgG isotype.

As used herein the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

In some embodiments, a subject antibody does not comprise a full-length immunoglobulin heavy chain and a full-length immunoglobulin light chain, and instead comprises antigen-binding fragments of a full-length immunoglobulin heavy chain and a full-length immunoglobulin light chain. In some embodiments, the antigen-binding fragments are contained on separate polypeptide chains; in other embodiments, the antigen-binding fragments are contained within a single polypeptide chain. The term "antigen-binding fragment" refers to one or more fragments of a full-length antibody that are capable of specifically binding to a non-contiguous apoE4 epitope as described above. Examples of binding fragments include (i) a Fab fragment (a monovalent fragment consisting of the VL, VH, CL and CH1 domains; (ii) a F(ab')$_2$ fragment (a bivalent fragment comprising two Fab fragments linked by a disulfide bridge at the hinge region; (iii) a Fd fragment (consisting of the VH and CH1 domains); (iv) a Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) diabodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). In some embodiments, a subject antibody fragment is a Fab fragment. In some embodiments, a subject antibody fragment is a single-chain antibody (scFv).

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

In some embodiments, a subject antibody comprises: a variable domain comprising: a) a heavy chain variable domain comprising: i. a CDR1 region that is identical in amino acid sequence to the heavy chain CDR1 region of 3H1; ii. a CDR2 region that is identical in amino acid sequence to the heavy chain CDR2 region of 3H1; and iii. a CDR3 region that is identical in amino acid sequence to the heavy chain CDR3 region of 3H1; and b) a light chain variable domain comprising: i. a CDR1 region that is identical in amino acid sequence to the light chain CDR1 region of 3H1; ii. a CDR2 region that is identical in amino acid sequence to the light chain CDR2 region of the 3H1; and iii. a CDR3 region that is identical in amino acid sequence to the light chain CDR3 region of 3H1; wherein the antibody specifically binds the above-described non-contiguous, conformational apoE epitope.

In certain embodiments, a subject antibody comprises: a) a variable domain comprising: i. a CDR1 region that is identical in amino acid sequence to the heavy chain CDR1 region of 3H1; ii. a CDR2 region that is identical in amino acid sequence to the heavy chain CDR2 region of 3H1; and iii. a CDR3 region that is identical in amino acid sequence to the heavy chain CDR3 region of 3H1; and b) a light chain variable domain comprising: i. a CDR1 region that is identical in amino acid sequence to the light chain CDR1 region of 3H1; ii. a CDR2 region that is identical in amino acid sequence to the light chain CDR2 region of 3H1; and iii. a CDR3 region that is identical in amino acid sequence to the light chain CDR3 region of 3H1; or b) a variant of the variable domain of part a) that is otherwise identical to the variable domain of part a) except for a number of (e.g., 1, 2, 3, 4, 5, 6, 7 or 8) amino acid substitutions in the CDR regions, where the antibody specifically binds the above-described non-contiguous, conformational apoE epitope.

In some embodiments, a subject synthetic antibody (e.g., a subject antibody that specifically binds non-contiguous epitope in apoE4, where the epitope comprises amino acid residues within amino acids 222-230 and 261-272 of apoE4) comprises: a) a light chain region comprising: i) one, two, or three complementarity determining regions (CDRs) from the 3H1 light chain variable region sequence; and ii) a light chain framework region from a human immunoglobulin light chain; and b) a heavy chain region comprising: i) one, two, or three CDRs from the 3H1 heavy chain variable region sequence; and ii) a heavy chain framework region from a human immunoglobulin heavy chain.

Examples of 3H1 light chain CDRs are: $V_L$ CDR1: RASQSISNNLH (SEQ ID NO:6); $V_L$ CDR2: YAYQSIS (SEQ ID NO:7); $V_L$ CDR3: QQSNSWPLT (SEQ ID NO:8). Examples of 3H1 heavy chain CDRs are: $V_H$ CDR1: GFTFSSYAMS (SEQ ID NO:2); $V_H$ CDR2: TISSGGSYTYYPDSVKG (SEQ ID NO:3); and $V_H$ CDR3: QFYYYGGSYDYFDY (SEQ ID NO:4). In some embodiments, any given CDR has a length that deviates from one of SEQ ID NOs:2, 3, 4, 6, 7, or 8 by 1 aa, 2 aa, 3 aa, 4 aa, or 5 aa. In some embodiments, any given CDR can vary in amino acid sequence from one of SEQ ID NOs:2, 3, 4, 6, 7, or 8 by 1, 2, 3, 4, or 5 conservative amino acid substitutions. A conservative amino acid substitution, for example, substitutes one amino acid for another of the same class (e.g., substitution of one hydrophobic amino acid, such as isoleucine, valine, leucine, or methionine, for another; or substitution of one polar amino acid for another, such as substitution of arginine for lysine, glutamic acid for aspartic acid, or glutamine for asparagine).

A subject synthetic antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 7A and set forth in SEQ ID NO:1, where SEQ ID NO:1 is the 3H1 heavy chain variable region amino acid sequence. A subject synthetic antibody can comprise a heavy chain variable region comprising one, two, or three of the heavy chain complementarity determining regions (CDRs) having a polypeptide sequence selected from one or more of SEQ ID NOs:2, 3, and 4, where SEQ ID NOs:2, 3, and 4 are the heavy chain CDR amino acid sequences.

In some embodiments, a subject synthetic antibody comprises a heavy chain variable region comprising one, two, or three of the heavy chain CDRs having a polypeptide sequence selected from one or more of SEQ ID NOs:2, 3, and 4; and FR regions that are human sequences (e.g., encoded by human heavy chain FR-encoding sequences). For example, in some embodiments, a subject synthetic antibody comprises a heavy chain variable region that comprises, in order from N-terminus to C-terminus: a human heavy chain FR1; a CDR1 comprising the amino acid sequence set forth in SEQ ID NO:2; a human heavy chain FR2; a CDR2 comprising the amino acid sequence set forth in SEQ ID NO:3; a human heavy chain FR3; a CDR3 comprising the amino acid sequence set forth in SEQ ID NO:4; and a human heavy chain FR4.

A subject synthetic antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 8A and set forth in SEQ ID NO:5, where SEQ ID NO:5 is the 3H1 light chain variable region amino acid sequence. A subject synthetic antibody can comprise a light chain variable region comprising one, two, or three of the light chain CDRs having the amino acid sequence set forth in SEQ ID NOs:6, 7, and 8, where SEQ ID NOs:6, 7, and 8 are the light chain CDR amino acid sequences.

In some embodiments, a subject synthetic antibody comprises a light chain variable region comprising one, two, or three of the light chain CDRs having a polypeptide sequence selected from one or more of SEQ ID NOs:6, 7, and 8; and FR regions that are human sequences (e.g., encoded by human light chain FR-encoding sequences). For example, in some embodiments, a subject synthetic antibody comprises a light chain variable region that comprises, in order from N-terminus to C-terminus: a human light chain FR1; a CDR1 comprising the amino acid sequence set forth in SEQ ID NO:6; a human light chain FR2; a CDR2 comprising the amino acid sequence set forth in SEQ ID NO:7; a human light chain FR3; a CDR3 comprising the amino acid sequence set forth in SEQ ID NO:8; and a human light chain FR4.

In some embodiments, a subject antibody comprises 3H1 heavy chain CDRs and 3H1 light chain CDRs in a single polypeptide chain, e.g., in some embodiments, a subject antibody is a scFv. In some embodiments, a subject antibody comprises, in order from N-terminus to C-terminus: a first amino acid sequence of from about 5 amino acids to about 25 amino acids in length; a CDR1 comprising the amino acid sequence set forth in SEQ ID NO:2; a second amino acid sequence of from about 5 amino acids to about 25 amino acids in length; a CDR2 comprising the amino acid sequence set forth in SEQ ID NO:3; a third amino acid sequence of from about 5 amino acids to about 25 amino acids in length; a CDR3 comprising the amino acid sequence set forth in SEQ ID NO:4; a fourth amino acid sequence of from about 5 amino acids to about 25 amino acids in length; a CDR1 comprising the amino acid sequence set forth in SEQ ID:6; a fifth amino acid sequence of from about 5 amino acids to about 25 amino acids in length; a CDR2 comprising the amino acid sequence set forth in SEQ ID NO:7; a sixth amino acid sequence of from about 5 amino acids to about 25 amino acids in length; a CDR3 comprising the amino acid sequence set forth in SEQ ID NO:8; and a seventh amino acid sequence of from about 5 amino acids to about 25 amino acids in length.

In some embodiments, a subject antibody comprises, in order from N-terminus to C-terminus: a light chain FR1 region; a CDR1 comprising the amino acid sequence set forth in SEQ ID NO:2; a light chain FR2 region; a CDR2 comprising the amino acid sequence set forth in SEQ ID NO:3; a light chain FR3 region; a CDR3 comprising the amino acid sequence set forth in SEQ ID NO:4; optionally a light chain FR4 region; a linker region; optionally a heavy chain FR1 region; a CDR1 comprising the amino acid sequence set forth in SEQ ID:6; a heavy chain FR2 region; a CDR2 comprising the amino acid sequence set forth in SEQ ID NO:7; a heavy chain FR3 region; a CDR3 comprising the amino acid sequence set forth in SEQ ID NO:8; and a heavy chain FR4 region. In some of these embodiments, each of the FR regions is a human FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO:22) and $GGGS_n$ (SEQ ID NO:23), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11 173-142 (1992)). Exemplary flexible linkers include, but are not limited GGSG (SEQ ID NO:24), GGSGG (SEQ ID NO:25), GSGSG (SEQ ID NO:26), GSGGG (SEQ ID NO:27), GGGSG (SEQ ID NO:28), GSSSG (SEQ ID NO:29), and the like. The ordinarily skilled artisan will recognize that design of a peptide conjugated to any elements described above can include linkers that are all or partially flexible, such that the linker can include a flexible linker as well as one or more portions that confer less flexible structure.

In some embodiments, a subject antibody is "humanized." The term "humanized antibody" refers to an antibody comprising at least one chain comprising variable region framework residues substantially from a human antibody chain (referred to as the acceptor immunoglobulin or antibody) and at least one CDR substantially from a mouse antibody, (referred to as the donor immunoglobulin or antibody). See, Queen et al., Proc. Natl. Acad. Sci. USA 86:10029 10033 (1989), U.S. Pat. Nos. 5,530,101, 5,585,089, 5,693,761, WO 90/07861, and U.S. Pat. No. 5,225,539. The constant region(s), if present, can also be substantially or entirely from a human immunoglobulin. In some embodiments, a subject antibody comprises one or more 3H1 CDRs and one or more FR regions from a human antibody. Methods of making humanized antibodies are known in the art. See, e.g., U.S. Pat. No. 7,256,273.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk JMB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, a subject antibody comprises scFv multimers. For example, in some embodiments, a subject antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to an the subject antibody that comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly (propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly (ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., comprise a covalently linked carbohydrate or polysaccharide moiety. Glycosylation of antibodies is typically either N-linked or O-linked N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one step reaction procedure in which the cross-linker is added to a solution containing a mixture of the polypeptides to be linked Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C or $^{32}$P), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. multistyrene, multipropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-dephenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2):209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., CYPYDVPDYA; SEQ ID NO:30), FLAG (e.g., DYKDDDDK; SEQ ID NO:31), c-myc (e.g., CEQKLISEEDL; SEQ ID NO:32), and the like; provide a detectable signal, e.g., an enzyme that generates a detectable product (e.g., (β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:33), HisX6 (HHHHHH) (SEQ ID NO:34), C-myc (EQKLISEEDL) (SEQ ID NO:35), Flag (DYKDDDDK) (SEQ ID NO:36), StrepTag (WSHPQFEK) (SEQ ID NO:37), hemagglutinin, e.g., HA Tag (YPYDVPDYA; SEQ ID NO:38), glutathinone-S-transferase (GST), thioredoxin, cellulose binding domain, RYIRS (SEQ ID NO:39), Phe-His-His-Thr (SEQ ID NO:40), chitin binding domain, S-peptide, T7 peptide, SH2 domain, C-end RNA tag, WEAAAREACCRECCARA (SEQ ID NO:41), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, 5100 proteins, parvalbumin, calbindin D9K, calbindin D28K, and calretinin, inteins, biotin, streptavidin, MyoD, leucine zipper sequences, and maltose binding protein.

A subject antibody will in some embodiments be fused to a polypeptide that binds to an endogenous blood brain barrier (BBB) receptor. Linking a subject antibody to a polypeptide that binds to an endogenous BBB receptor facilitates crossing the BBB, e.g., in a subject treatment method (see below) involving administration of a subject antibody to an individual in need thereof. Suitable polypeptides that bind to an endogenous BBB include antibodies, e.g., monoclonal antibodies, or antigen-binding fragments thereof, that specifically bind to an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-deaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or N(R)$_2$ moieties, wherein R is H, (C$_1$-C$_4$) alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

Methods of Producing a Subject Antibody

A subject antibody can be produced by any known method, e.g., conventional synthetic methods for protein synthesis; recombinant DNA methods; etc.

Where a subject antibody is a single chain polypeptide, it can synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. Saccharomyces (e.g., *S. cerevisiae*) and Pichia are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148:1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as TWEEN-20™, etc.; a protease inhibitor; glycerol; and the like.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

In some embodiments, a subject nucleic acid comprises a nucleotide sequence having at least about 75%, at least about 80%, at least about 85%, at least about 90%, at least about 95%, at least about 98%, at least about 99%, or 100%, with SEQ ID NO:9 (FIG. 7B). In some embodiments, a subject nucleic acid comprises a nucleotide sequence having at least about 75%, at least about 80%, at least about 85%, at least about 90%, at least about 95%, at least about 98%, at least about 99%, or 100%, with SEQ ID NO:10 (FIG. 8B). In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 7B that encodes SEQ ID NO:2. In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 7B that encodes SEQ ID NO:3. In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 7B that encodes SEQ ID NO:4. In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 7A that encodes SEQ ID NOs:2, 3, and 4.

In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 8B that encodes SEQ ID NO:6. In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 8B that encodes SEQ ID NO:7. In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 8B that encodes SEQ ID NO:8. In some embodiments, a subject nucleic acid comprises a nucleotide sequence having at least about 75%, at least about 80%, at least about 85%, at least about 90%, at least about 95%, at least about 98%, at least about 99%, or 100%, the nucleotide sequence depicted in FIG. 8B that encodes SEQ ID NOs:6, 7, and 8.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) Vaccine 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as Escherichia coli include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art;

many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject antibody. A subject nucleic acid can comprise a nucleotide sequence encoding heavy-and light-chain 3H1 CDRs. In some embodiments, a subject nucleic acid comprises a nucleotide sequence encoding heavy- and light-chain 3H1 CDRs, where the CDR-encoding sequences are interspersed with FR-encoding nucleotide sequences. In some embodiments, the FR-encoding nucleotide sequences are human FR-encoding nucleotide sequences.

In some embodiments, a subject nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in FIG. 7B. In some embodiments, a subject nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in FIG. 8B.

Cells

The present disclosure provides isolated genetically modified host cells (e.g., in vitro cells) that are genetically modified with a subject nucleic acid. In some embodiments, a subject isolated genetically modified host cell can produce a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica,*

Pichia trehalophila, Pichia koclamae, Pichia membranaefaciens, Pichia opuntiae, Pichia thermotolerans, Pichia salictaria, Pichia guercuum, Pichia ptjperi, Pichia stiptis, Pichia methanolica, Pichia sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii,* and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable Shigella strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Compositions

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in an amyloid plaque, amelioration of a symptom of an apoE4-associated disorder, improvement in cognitive function, etc. Generally, the desired result is at least a reduction in a symptom of an apoE4-associated disorder, as compared to a control. A subject antibody can be delivered in such a manner as to avoid the blood-brain barrier, as described in more detail below. A subject antibody can be formulated and/or modified to enable the antibody to cross the blood-brain barrier.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-Methylglucosamine, galactosamine, and neuraminic acid; and/or non-ionic surfactants such as Tween, Brij Pluronics, Triton-X or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark TWEEN 20™) and polysorbate 80 (sold under the trademark TWEEN 80™). Examples of suitable polyethylene-polypropylene copolymers are those sold under the names PLURONIC™ F68 or POLOXAMER 188™. Examples of suitable Polyoxyethylene alkyl ethers are those sold under the trademark BRIJ™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% TWEEN 20™ w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% TWEEN 20™ w/v; 20 mM L-histidine; and 250 mM sucrose; and has a pH of 5.5; or 2) 75 mg/mL of a subject antibody; 0.04% TWEEN 20™ w/v; 20 mM L-histidine; and 250 mM sucrose; and has a pH of 5.5;or 3) 75 mg/mL of a subject antibody; 0.02% TWEEN 20™ w/v; 20 mM L-histidine; and 250 mM Sucrose; and has a pH of 5.5; or 4) 75 mg/mL of a subject antibody; 0.04% TWEEN 20™ w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising:1) 7.5 mg/mL of a subject antibody; 0.022% TWEEN 20™ w/v; 120 mM L-histidine; and 250 125 mM sucrose; and has a pH of 5.5; or 2) 37.5 mg/mL of a subject antibody; 0.02% TWEEN 20™ w/v; 10 mM L-histidine; and 125 mM sucrose; and has a pH of 5.5; or 3) 37.5 mg/mL of a subject antibody; 0.01% TWEEN 20™ w/v; 10 mM L-histidine; and 125 mM sucrose; and has a pH of 5.5; or 4) 37.5 mg/mL of a subject antibody; 0.02% TWEEN 20™ w/v; 10 mM L-histidine; 125 mM trehalose; and has a pH of 5.5; or 5) 37.5 mg/mL of a subject antibody; 0.01% TWEEN 20™ w/v; 10 mM L-histidine; and 125 mM trehalose; and has a pH of 5.5; or 6) 5 mg/mL of a subject antibody; 0.02% TWEEN 20™ w/v; 20 mM L-histidine; and 250 mM trehalose; and has a pH of 5.5; or 7) 75 mg/mL of a subject antibody; 0.02% TWEEN 20™ w/v; 20 mM L-histidine; and 250 mM mannitol; and has a pH of 5.5; or 8) 75 mg/mL of a subject antibody; 0.02% TWEEN 20™ w/v; 20 mM L histidine; and 140 mM sodium chloride; and has a pH of 5.5;or 9) 150 mg/mL of a subject antibody; 0.02% TWEEN 20™ w/v; 20 mM L-histidine; and 250 mM trehalose; and has a pH of 5.5; or 10) 150 mg/mL of a subject antibody; 0.02% TWEEN 20™ w/v; 20 mM L-histidine; and 250 mM mannitol; and has a pH of 5.5; or 11) 150 mg/mL of a subject antibody; 0.02% TWEEN 20™ w/v; 20 mM L-histidine; and 140 mM sodium chloride; and has a pH of 5.5; or 12) 10 mg/mL of a subject antibody; 0.01% TWEEN 20™ w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with the subject invention. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(-)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.). Some of these formulations will now be discussed in more detail.

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an apoE4-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site (e.g., a brain region containing amyloid plaques), e.g., by biolistic delivery to the target site.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of a subject antibody, e.g. in oral or injectable doses, are provided.

In such kits, in addition to the containers containing the unit doses will be an informational package insert describing the use and attendant benefits of the antibody in treating pathological condition of interest. Preferred compounds and unit doses are those described herein above.

Treatment Methods

The present disclosure provides methods of treating a disorder associated with apoE, the methods generally involving administering to an individual in need thereof (e.g., an individual having a disorder associated with apoE) an effective amount of a subject antibody, alone (e.g., in monotherapy) or in combination (e.g., in combination therapy) with one or more additional therapeutic agents.

The present disclosure provides a method of reducing binding of apoE4 to an amyloid-beta polypeptide in the brain of an individual, the method generally involving administering to an individual in need thereof an effective amount of a subject antibody. For example, in some embodiments, an effective amount of a subject antibody is an amount that reduces apoE4-Aβ binding by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of binding between apoE4 and Aβ in the absence of the antibody.

The present disclosure provides a method of blocking the C-terminal cleavage of apolipoprotein E4 in the brain of an individual, the method generally involving administering to an individual in need thereof an effective amount of a subject antibody. For example, in some embodiments, an effective amount of a subject antibody is an amount that reduces C-terminal cleavage of apoE4 by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of cleavage of apoE4 by the AECE in the absence of the antibody.

In some embodiments, an effective amount of a subject antibody is an amount that, when administered alone (e.g., in monotherapy) or in combination (e.g., in combination therapy) with one or more additional therapeutic agents, in one or more doses, is effective to reduce an adverse symptom of an apoE-related disorder by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the severity of the adverse symptom in the absence of treatment with the antibody.

In some embodiments, an effective amount of a subject antibody is an amount that, when administered alone (e.g., in monotherapy) or in combination (e.g., in combination therapy) with one or more additional therapeutic agents, in one or more doses, is effective to improve cognitive function in the individual being treated. For example, an effective amount of a subject antibody can improve cognitive function in an individual by at least about 5%, at least about 10%, at least about 15%, at least about 20%, at least about 25%, at least about 30%, at least about 40%, at least about 50%, or more, compared to cognitive function in the absence of treatment with the antibody.

In other embodiments, the present disclosure provides methods for inhibiting formation of neurofibrillary tangles in an individual, comprising administering an effective amount of a subject antibody to the individual. Whether formation of neurofibrillary tangles is inhibited can be determined, e.g., in experimental animal models of AD. Experimental animal models of AD have been described in the art; any known animal model of AD can be used to determine whether an agent of the invention inhibits formation of neurofibrillary tangles. See, e.g., U.S. Pat. No. 6,046,381. Such animal models can also be used to determine whether other phenomena, such as amyloid deposition, and cognitive abilities, are affected by a subject antibody. Whether a subject antibody reduces formation of neurofibrillary tangles and/or Aβ deposits can also be determined in humans using any known method, including, but not limited to, immunohistochemical staining of brain biopsy samples.

In other embodiments, the present disclosure provides methods for treating AD, comprising administering to an individual an effective amount of a subject antibody. Individuals known to be at risk of developing AD are amenable to treatment using a subject method. Thus, a subject antibody is suitable for prophylactic use in patients who are heterozygous or homozygous for apoE4 but do not show overt symptoms of Alzheimer's disease or other neurodegenerative disorders. The methods are also useful to treat an individual who already displays symptoms of AD, where the method treats AD by reducing advancement of the disease, or reduces severity of a symptom associated with AD. Whether advancement of AD is reduced or severity of an AD-related symptom is reduced can be determined by assessing any symptom or parameter associated with AD, including, but not limited to, cognitive function, and memory. Such determinations are well within the ability of those skilled in the art using standard methods known in the art.

Combination Therapy

In some embodiments, a subject treatment method involves administering a subject antibody and one or more additional therapeutic agents. Suitable additional therapeutic agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

In some embodiments, a subject combination therapy comprises administration of effective amounts of a subject antibody and an agent that inhibits apoE4 domain interaction (e.g., an agent as described in U.S. Patent Publication No. 2006/0073104); and in Ye et al. (2005) *Proc. Natl. Acad. Sci. USA* 102:18700.

In some embodiments, a subject combination therapy comprises administration of effective amounts of a subject antibody and an acetylcholinesterase inhibitor. In some embodiments, a subject combination therapy comprises administration of effective amounts of a subject antibody and an anti-inflammatory agent.

Subjects Suitable for Treatment

A variety of subjects are suitable for treatment with a subject method. Suitable subjects include any individual, particularly a human, who has an apoE4-associated disorder, who has been diagnosed with an apoE4-associated disorder, who is at risk for developing an apoE4-associated disorder, who has had an apoE-associated disorder and is at risk for recurrence of the apoE4-associated disorder, or who is recovering from an apoE4-associated disorder.

Subjects suitable for treatment with a subject method include individuals who have one apoE4 allele; and individuals who have two apoE4 alleles. In other words, suitable subjects include those who are homozygous for apoE4 and those who are heterozygous for apoE4. For example, an individual can have an apoE3/apoE4 genotype, or an apoE4/apoE4 genotype. In some embodiments, the subject has been diagnosed as having Alzheimer's disease.

Detection Methods

The present disclosure provides various detection methods that involve use of a subject antibody. Detection methods include diagnostic methods, prognostic methods, and monitoring methods. A subject detection method generally involves detecting in a brain tissue of an individual an apoE that exhibits an epitope that is recognized by a subject antibody.

A subject detection method can be carried out in vitro on a biological sample obtained from an individual. Thus, the present disclosure provides a method of detecting a pathological form of apolipoprotein E in a biological sample, the method comprising: a) contacting the biological sample in vitro with a subject antibody; and b) detecting binding, if any, of the synthetic antibody to an epitope present in the sample. The biological sample can be, e.g., a brain sample obtained from an individual post-mortem.

In some embodiments, a subject detection method involves administering a subject antibody to an individual, and detecting binding of the antibody to a brain tissue in the individual, e.g., to an amyloid plaque in the individual. In some embodiments, the antibody will be detectably labeled. The individual can be a living individual. In some embodiments, the antibody is detectably labeled. In some embodiments, the antibody is modified to cross the blood-brain bather (BBB). In some embodiments, the antibody is administered systemically (e.g., intravenously).

As noted above, the antibody can be detectably labeled; binding of the antibody to brain tissue in the individual can be detected using a method that is appropriate to the detectable label. For example, the antibody can comprise a contrast agent or a radioisotope. The detecting step can include diagnostic imaging (e.g., positron emission tomography (PET), gamma-scintigraphy, single photon emission computerized tomography (SPECT), magnetic resonance imaging (MRI), functional magnetic resonance imaging (fMRI), or magnetoencephalography). Magnetic resonance imaging is used in some embodiments. The antibody can be labeled with a contrast agent (e.g., gadolinium, dysprosium, or iron). In some embodiments, the antibody is labeled with gadolinium.

In some embodiments, a subject method is a diagnostic method, e.g., to determine whether an individual has an apoE4-associated disorder. A level of binding of a subject antibody to a brain tissue that is higher than a control level of binding indicates that the individual has an apoE4-associated disorder.

In some embodiments, a subject method is a monitoring method, e.g., an individual who has been diagnosed as having an apoE4-associated disorder, and is being treated for the disorder, is monitored for response to the treatment and/or progression/regression of the disorder. In these embodiments, a subject antibody is administered to an individual, and binding of the antibody to tissues (e.g., a brain tissue) in the individual is detected, as described above. For example, a subject detection method (as described above) can be carried out on an individual before the individual is treated for the apoE4-associated disorder and/or after the individual has begun treatment for the disorder. For example, a subject detection method can be carried out on an individual one day, one week, one month, two months, three months, six months, or more than six months, following the beginning of treatment for an apoE4-associated disorder. A subject detection method can be carried out more than once on an individual following the beginning of treatment for an apoE4-associated disorder. Detection of binding of a subject antibody to brain tissue in the individual can provide an indication of the efficacy of the treatment. As an example, detection of binding of a subject antibody to brain tissue in the individual can indicate that a treatment is highly efficacious and should be continued. As another example, detection of binding of a subject antibody to brain tissue in the individual can indicate that a treatment is moderately efficacious; and a decision can be made as to whether the treatment should be continued, the dosing regimen should be modified, or the drug being administered should be changed.

Kits

The present disclosure provides a kit (e.g., a test kit) that includes a subject antibody. A subject kit is useful in carrying out a subject detection method.

A subject kit can include one or more of: a subject antibody, a nucleic acid encoding the same, or a cell comprising a subject nucleic acid. The subject antibody in a subject kit can be humanized. A subject kit can include reagents for labeling the antibody. In some embodiments, the antibody in a subject kit comprises a detectable label.

Other optional components of the kit include: a buffer; a protease inhibitor; a detectable label; etc. Where a subject kit comprises a subject nucleic acid, the nucleic acid may also have restrictions sites, multiple cloning sites, primer sites, etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Characterization of 3H1 Monoclonal Antibody

As shown below, a unique conformation of the lipid-binding domain recognized by an apoE-specific monoclonal antibody, 3H1, determines the isoform-dependent interaction of apoE with Aβ. This conformation is assumed to a greater extent by apoE4 than apoE3 and is modified by lipid binding.

The 3H1 antibody recognizes apoE in the center of amyloid plaques in AD brains and blocks the interaction between apoE and Aβ in vitro, suggesting that this unique conformation of the lipid-binding domain of apoE is important in the nucleation of amyloid plaque formation in AD brains.

Materials and Methods

Reagents. Minimum essential medium (MEM), N2 medium supplements, and fetal bovine serum were from Invitrogen (Rockville, Md.). Polyclonal goat anti-human apoE was from Calbiochem (San Diego, Calif.). Monoclonal antibody 3H1 was kindly provided by Dr. Ross W. Milne (University of Ottawa Heart Institute, Canada). The anti-mouse and anti-goat IgG coupled to fluorescein and Texas Red were from Vector Laboratories (Burlingame, Calif.). Horseradish peroxidase-coupled anti-mouse and anti-goat IgG were from Dako (Carpinteria, Calif.). ECL was from Amersham Biosciences (Arlington Heights, Ill.). The recombinant human apoE3 and apoE4 were kindly provided by Dr. Karl Weisgraber at the Gladstone Institute of Neurological Disease (San Francisco, Calif.). $A\beta_{1-42}$ peptide was from Biopeptides (San Diego, Calif.) and monomers were prepared as described (Stine et al., 2003).

cDNA constructs. Polymerase chain reaction (PCR) products encoding apoE3, apoE4, or fragments of apoE with its signal peptide were subcloned into a pcDNA 3.1(+) vector (Invitrogen) containing the cytomegalovirus promoter. Complementary DNA (cDNA) constructs encoding apoE3 or apoE4 with various mutations or insertions were made from the pcDNA—apoE3 or pcDNA—apoE4 construct with a QuikChange kit (Stratagene). All constructs were confirmed by sequence analysis.

Cell culture, transfection, and western blotting. Mouse neuroblastoma (Neuro-2a) and astrocytic (C6) cells (American Type Culture Collection, Manassas, Va.) maintained at 37° C. in MEM containing 10% fetal bovine serum (FBS) were transiently transfected with different apoE cDNA constructs using Lipofectamine 2000 (Invitrogen) (Huang et al., 2001). Neuro-2a cells expressing different forms of apoE were collected in a low-detergent lysis buffer, separated by sodium dodecyl sulfate-polyacrylamide gel electrophoresis (SDS-PAGE), and immunoblotted for apoE with polyclonal and monoclonal antibodies, as described (Huang et al., 2001).

Preparation of apoE and DMPC complex. Dimyristoyl phosphatidylcholine (DMPC) (Avanti Polar Lipids, Alabaster, Ala.) was used at a concentration of 20 mg/ml dissolved into phosphate-buffered saline (PBS). DMPC solution was sonicated for 6 min per cycle until the solution became clear and centrifuged at 14,000 rpm for 2 min to pellet debris. ApoE was then added to obtain various final stock concentrations and allowed to incubate at 23.7° C. overnight before use in enzyme-linked immunosorbent assay (ELISA) experiments.

ApoE ELISA. ApoE3 or apoE4 was diluted to 1 μg/ml in PBS and 50 ng was used to coat 96-well flat-bottom immuno plates (Nunc) overnight at 4° C. Wells were washed several times with wash buffer (PBS containing 0.1% bovine serum albumin (BSA)) and blocked for 1 h with 4% BSA in PBS. All incubations were performed at room temperature. Primary antibodies (polyclonal anti-apoE or 3H1) were diluted in blocking buffer and incubated for 1 h. Secondary antibodies against goat or mouse IgG labeled with horse radish peroxidase (HRP) diluted in blocking buffer were added to the wells after several washes and incubated for 1 h. Tert-butyl methylether (TMBE) substrate (Thermo-Pierce) was used to visualize the amount of bound secondary antibody at 450 nm on a SpectraMax190 plate reader (Molecular Devices) using Softmax Pro software for data collection.

ApoE and Aβ binding assay. $A\beta_{1-42}$ (Biopeptides) was used to coat the surface of a 96-well plate at 330 ng/well and ELISA was performed essentially as described above. Briefly, after blocking for 1 h and several rinses, bound apoE3 or apoE4 was detected with a polyclonal apoE antibody (Calbiochem), which was determined in this study to have no difference in affinity for apoE3 or apoE4. For the apoE/Aβ binding inhibition ELISA, apoE3 or apoE4 was pre-incubated with purified 3H1 IgG at decreasing concentrations for 1 h in blocking buffer. The amounts of apoE3 or apoE4 used were based on their equimolar ratios for binding affinity with Aβ. ApoE/3H1 mixture was added to the Aβ-coated wells and allowed to incubate for 1 h. Subsequent detection of apoE bound with Aβ was performed with polyclonal anti-apoE, as stated above.

Immunocytochemistry, immunohistochemistry, and confocal microscopic analysis. Neuro-2a and C6 cells transiently transfected with various apoE cDNA constructs were grown in serum-free MEM for 18-24 h, fixed in 3% paraformaldehyde for 15-20 min at 4° C., permeabilized for 45 min at room temperature with 0.5% Tween-20 in PBS (Du et al., 1998), and stained with polyclonal anti-apoE (1:4000) or monoclonal anti-apoE (3H1, 1:1000) and a fluorescein-coupled secondary antibody (Vector Laboratories) (Huang et al., 2001). Labeled cells were mounted in VectaShield (Vector Laboratories) and viewed with a Radiance 2000-laser-scanning confocal system (Bio-Rad) mounted on an Optiphot-2 microscope (Nikon). Some Neuro-2a and C6 cells were cotransfected with various apoE cDNA constructs and a construct encoding green fluorescent protein fused with an endoplasmic reticulum or a Golgi apparatus localization signal peptide (BD Biosciences), stained with polyclonal or monoclonal anti-apoE and immunofluorescently labeled secondary antibodies, and analyzed by confocal microscopy.

For immunohistochemistry, brain tissues from AD patients and age-matched controls were fixed in 3% paraformaldehyde, sectioned with a vibratome, and stained with polyclonal and monoclonal anti-apoE and anti-Aβ antibodies (Buttini et al., 1999; Huang et al., 2001; Harris et al., 2003; Brecht et al., 2004). To block nonspecific reactions, all sections were incubated for 1 hr with 10% normal serum/PBS from the same species that produced the secondary antibodies (Jackson ImmunoResearch, West Grove, PA) followed by a 1-h incubation with primary antibody. Sections were washed three times and incubated for 1 hr with the corresponding secondary antibodies labeled with fluorescein or Texas Red (Vector). After three washes in PBS, the sections were mounted in VectaShield (Vector) and viewed with a Radiance 2000 laser-scanning confocal system (Bio-Rad, Hercules, CA) mounted on an Optiphot-2 microscope (Nikon, Tokyo, Japan).

Statistical Analysis. Values are expressed as mean ±SD. The statistical significance of the difference between means was assessed by unpaired, two-sample t tests. The statistical significance of the difference among means was assessed by ANOVA. $p<0.05$ was considered statistically significant.

Results

Differential reactivity of the monoclonal antibody 3H1 with apoE3 and apoE4

The apoE-specific monoclonal antibody 3H1 was generated over 20 years ago (Weisgraber et al., 1986). Its epitope is located between residues 244 and 272 (FIG. 1A) (Weisgraber et al., 1986), within the lipid binding domain of apoE (Weisgraber, 1994). Using an enzyme-linked immunosorbent assay (ELISA), in which apoE3 or apoE4 was coated to the surface of a 96-well plate and 3H1 was used as the primary detecting antibody, it was found that 3H1 has a much higher reactivity (9±1-fold) with apoE4 than with apoE3 (FIG. 1B). In a control experiment, a polyclonal apoE antibody had nearly overlapping reaction curves for apoE3 and apoE4, indicating similar affinity for the two isoforms and confirming the identical coating of the two proteins (FIG. 1C). Furthermore, in a competitive ELISA in which different amounts of free apoE3 or apoE4 were preincubated with the same amount of 3H1 before addition into apoE4-coated wells, apoE4 exhibited a higher reactivity with 3H1 (FIG. 1D). These results suggest that the 3H1-epitope is more exposed or accessible in apoE4 or that 3H1 recognizes a unique conformation that apoE4 assumes to a greater extent than apoE3.

The N- and C-Terminal Sequences of apoE Modulate its Interaction with 3H1

The reactivity of N-terminal 22-kDa (aal-191) and C-terminal 10-kDa (aa222-299) fragments of apoE with 3H1 was tested in the ELISA. The N-terminal 22-kDa fragment of apoE3 or apoE4, which lacks the lipid-binding domain, did not react with 3H1 (Weisgraber et al., 1986). Surprisingly, the C-terminal 10-kDa fragment, which contains the lipid-binding domain, had a much lower reactivity with 3H1 than full-length apoE3 or apoE4 (FIG. 1E), suggesting that the N-terminal sequence of apoE modulates the reactivity of the lipid-binding domain with 3H1. Deletion of the last 27 amino acids from the C-terminal (10-kDa) fragment (apoE(222-272)) dramatically increased its reactivity with 3H1 (FIG. 1E), indicating that the C-terminal sequence (aa273-299) also has a modulatory effect. These results suggest that 3H1 recognizes a unique conformation of the lipid-binding domain, which is modified by both the N-and C-terminal sequences of apoE, and that apoE4 assumes this conformation to a greater extent than apoE3.

FIGS. 1A-E. Differential reactivity of 3H1 with apoE3 and apoE4. A, A schematic of different functional domains of human apoE. B,C, Recombinant full-length apoE3 or apoE4 was coated onto 96-well microtiter plates (50 ng/well) and detected with 3H1 (B) or polyclonal anti-apoE (Poly Anti-E) (C) at different concentrations in an ELISA. D, A competitive ELISA, in which different amounts of recombinant apoE3 or apoE4 were preincubated with the same amount of 3H1 IgG at room temperature for 1 h and then added to the apoE4-coated wells. E, Recombinant apoE3, apoE4, and apoE fragments were coated onto 96-well microtiter plates (50 ng/well) and detected with 3H1 at different concentrations in an ELISA. All experiments were performed in triplicate. Values are mean±SD. OD, optical density.

Lipid Modification of the Reactivity of apoE to 3H1

Figure 2:
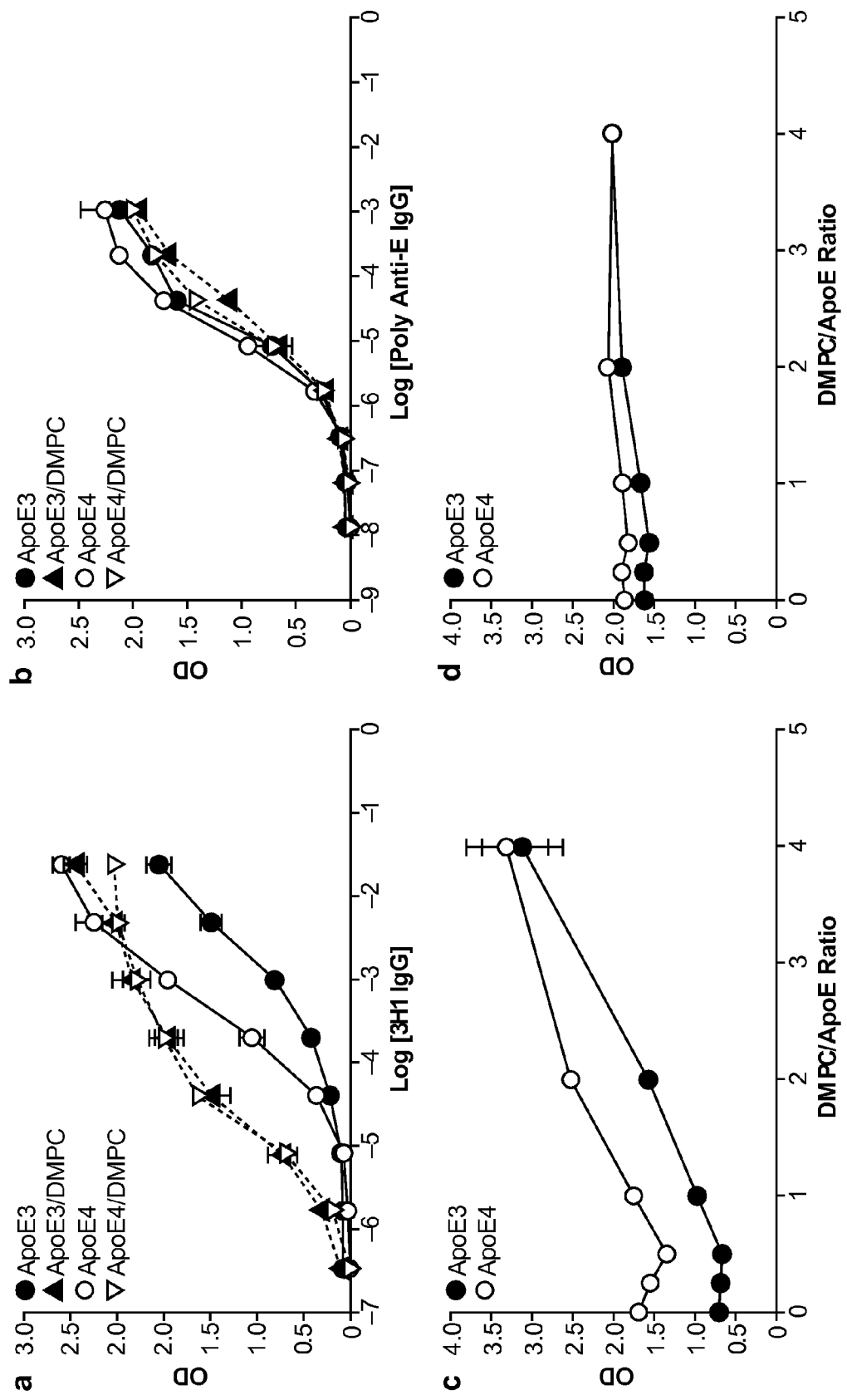
FIGS. 2A-D depict lipid modification of 3H1 reactivity with apoE.

Next, it was determined whether lipid binding modifies the reactivity of apoE with 3H1. Lipid binding (DMPC:apoE=4:1) greatly increased the reactivity of both apoE3 (-120-fold) and apoE4 (~20-fold), abolishing the difference between them (FIG. 2A). Lipid binding did not significantly alter the reactivity of either isoform with a polyclonal apoE antibody (FIG. 2B). Furthermore, the lipid modification was dose-dependent for 3H1 (FIG. 2C) but not for the polyclonal antibody (FIG. 2D). Thus, lipid binding increases 3H1 reactivity and abolishes the difference between apoE3 and apoE4, possibly by causing them to adopt the conformation recognized by 3H1.

FIGS. 2A-D. Lipid modification of 3H1 reactivity with apoE. Lipid-free and DMPC-lipidated (DMPC:apoE=4:1) apoE3 and apoE4 were coated onto 96-well microtiter plates (50 ng protein/well) and detected with 3H1 (A) or polyclonal anti-apoE (B) at different concentrations in an ELISA. C,D, ApoE3 or apoE4 lipidated with different amounts of DMPC was coated onto 96-well microtiter plates (50 ng protein/well) and detected with 3H1 (C) or polyclonal anti-apoE (D) at different concentrations in an ELISA. All experiments were performed in triplicate. Values are mean±SD. OD, optical density.

Figure 3:
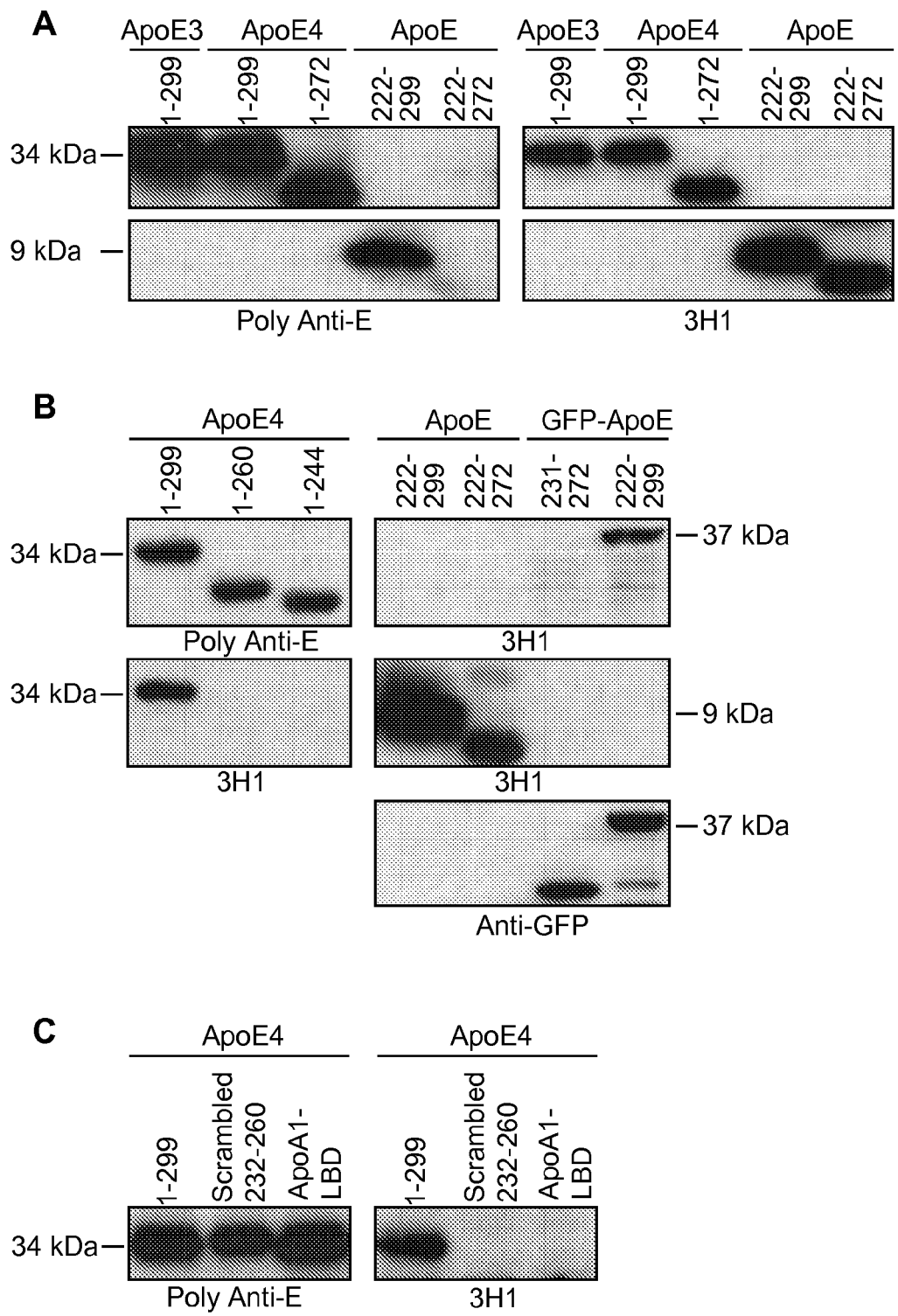
FIGS. 3A-C depict 3H1 detection of a discontinuous epitope in the lipid binding domain of apoE.

3H1 Recognizes a Unique Conformation of a Discontinuous Epitope in the Lipid-Binding Domain of apoE To characterize the 3H1 epitope in more detail, the reactivity of 3H1 with different fragments of apoE was tested by western blot. 3H1 detected apoE3(1-299), apoE4(1-299), apoE4(1-272), and apoE(222-299) (FIG. 3A). Western blot analysis confirmed that 3H1 recognizes the sequence between residues 222 and 272 (FIG. 3A). However, 3H1 did not detect apoE(1-240) or apoE(1-260) (FIG. 3B), suggesting that residues 261-272 are critical for 3H1 recognition. Additionally, although 3H1 reacted with apoE(222-272), apoE (222-299), and GFP-apoE(222-299), it did not detect green fluorescent protein-apoE (231-272) (GFP-apoE(231-272)) (FIG. 3B), suggesting that residues 222-230 are also critical. GFP-apoE(231-272) was used to control for adequate protein expression by anti-GFP western blot (FIG. 3B) due to a lack of detection of apoE(222-272) (FIG. 3A) or apoE(231-272) by polyclonal anti-apoE. Additionally, GFP-apoE(222-299) was used to demonstrate that the GFP tag itself did not alter 3H1 detection of the apoE fragment (FIG. 3B). Since aa222-230 and aa261-272 are critical for 3H1 recognition and are 30 residues apart, they must therefore reside in close proximity within a three-dimensional structure to form a discontinuous 3H1-epitope.

To determine whether the 30 amino acids between residues 231 and 260 play a role in 3H1 reactivity or function as a linker for the discontinuous 3H1 epitope, the 30 amino acids between residues 231 and 260 were replaced with a similar sequence from the lipid-binding region of apoAl (Frank and Marcel, 2000) or with a scrambled sequence. Both replacements abolished 3H1 reactivity with apoE4 (FIG. 3C), suggesting that the sequence of aa 231-260 helps maintain the discontinuous epitope in a 3H1-recognizable conformation.

FIGS. 3A-C. 3H1 detects a discontinuous epitope in the lipid binding domain of apoE. A, The reactivity of 3H1 and polyclonal anti-apoE with apoE3(1-299), apoE4(1-299), apoE4(1-272), apoE(222-272), and apoE(222-299) was determined by western blot. B, The reactivity of 3H1 and/or polyclonal anti-apoE with apoE4(1-299), apoE4(1-260), apoE4(1-244), GFP-apoE(231-272), and GFP-apoE(222-299) from transiently transfected Neuro-2a cells was determined by western blot. C, 3H1 and polyclonal anti-apoE western blot of apoE with mutations that replaced the lipid binding domain (LBD) of apoE with a scrambled sequence or with the LBD of apoAl.

3H1 Only Recognizes a Minor Population of apoE in Human Brains

Figure 4:
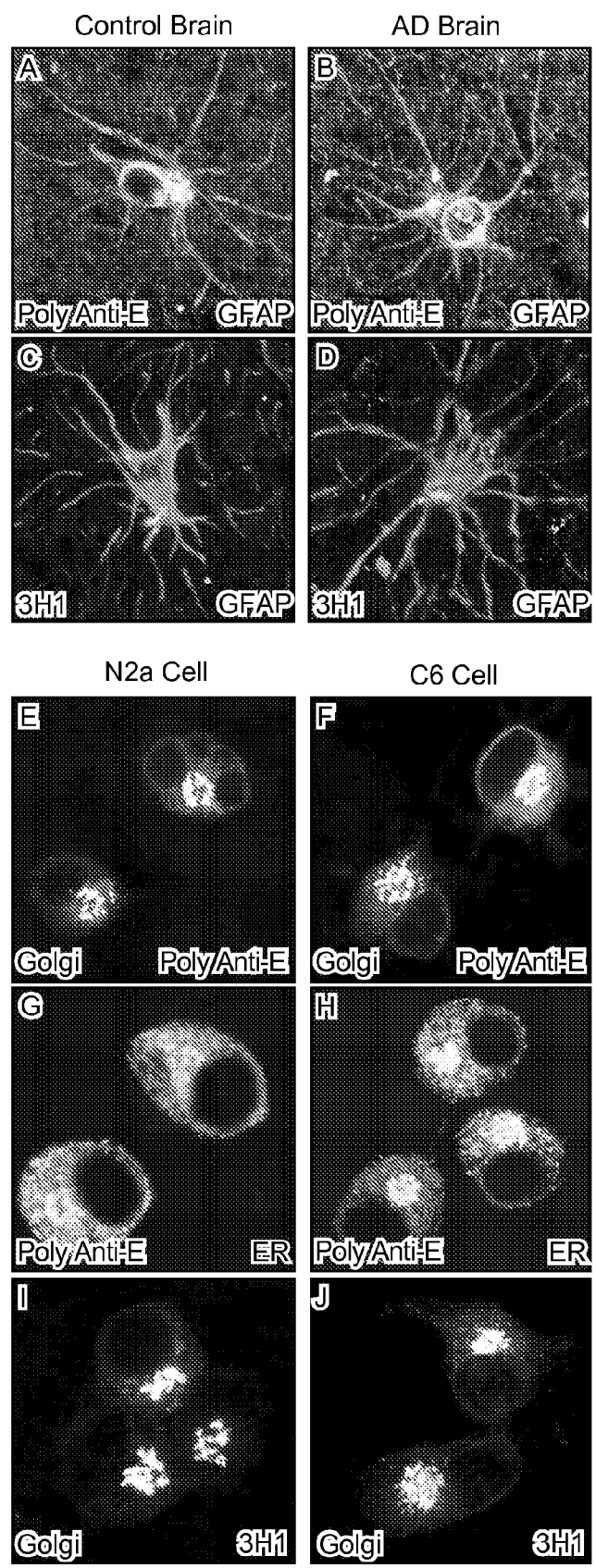
FIGS. 4A-J depict 3H1 recognition of apoE in human brains.

To assess the physiological or neuropathological relevance of the 3H1-recognizable conformation of apoE in vivo, the reactivity of 3H1 and a polyclonal antibody with apoE in human brains (AD cases and controls) was compared by immunofluorescence staining The polyclonal antibody recognized apoE within astrocytes, shown by costaining with antibody to glial fibrillary acid protein (anti-GFAP), and secreted apoE, as indicated by the bright apoE staining across the tissue section, in both control (FIG. 4A) and AD brains (FIG. 4B). Conversely, 3H1 detected very poorly astrocytic and secreted apoE in both control (FIG. 4C) and AD brains (FIG. 4D). However, in some astrocytes, a small area within the cell body was stained brightly with 3H1 (FIG. 4C,D), which resembled the Golgi apparatus.

To test this possibility, astrocytic C6 and neuronal Neuro-2a cells stably expressing apoE4 and transiently expressing either a Golgi apparatus or an endoplasmic reticulum (ER)

marker were immunostained. Polyclonal anti-apoE recognized apoE in both the Golgi apparatus and the ER in both cell types (FIG. 4E-H), while 3H1-positive apoE colocalized only with the Golgi apparatus marker (FIG. 4I,J). These results suggest that 3H1 preferably detects apoE in the Golgi apparatus, which may be related to the increased lipidation state of apoE in this subcellular compartment, and that a large proportion of apoE in human brains and in cultured neuronal or astrocytic cells does not assume or maintain a 3H1-positive conformation.

FIGS. 4A-J. 3H1 only recognizes a minor population of apoE in human brains. A-D, Control and AD brain sections were co-immunostained for the astrocytic marker glial fibrillary acid protein (GFAP) (red) and polyclonal anti-apoE (green) (A,B) or 3H1 (green) (C,D). E,F, Neuro-2a and astrocytic C6 cell lines stably expressing apoE were transfected with a Golgi-enhanced GFP (EGFP) marker and immunostained with polyclonal anti-apoE (red). G,H, Neuro-2a and astrocytic C6 cell lines stably expressing apoE were transfected with a dsRed-endoplasmic reticulum (ER) marker and immunostained with polyclonal anti-apoE (green). I,J, Neuro-2a and astrocytic C6 cell lines stably expressing apoE were transfected with a Golgi-EGFP marker and immunostained with 3H1 (red).

3H1 Only Recognizes apoE in the Center of Amyloid Plaques in Human AD Brains

Figure 5:
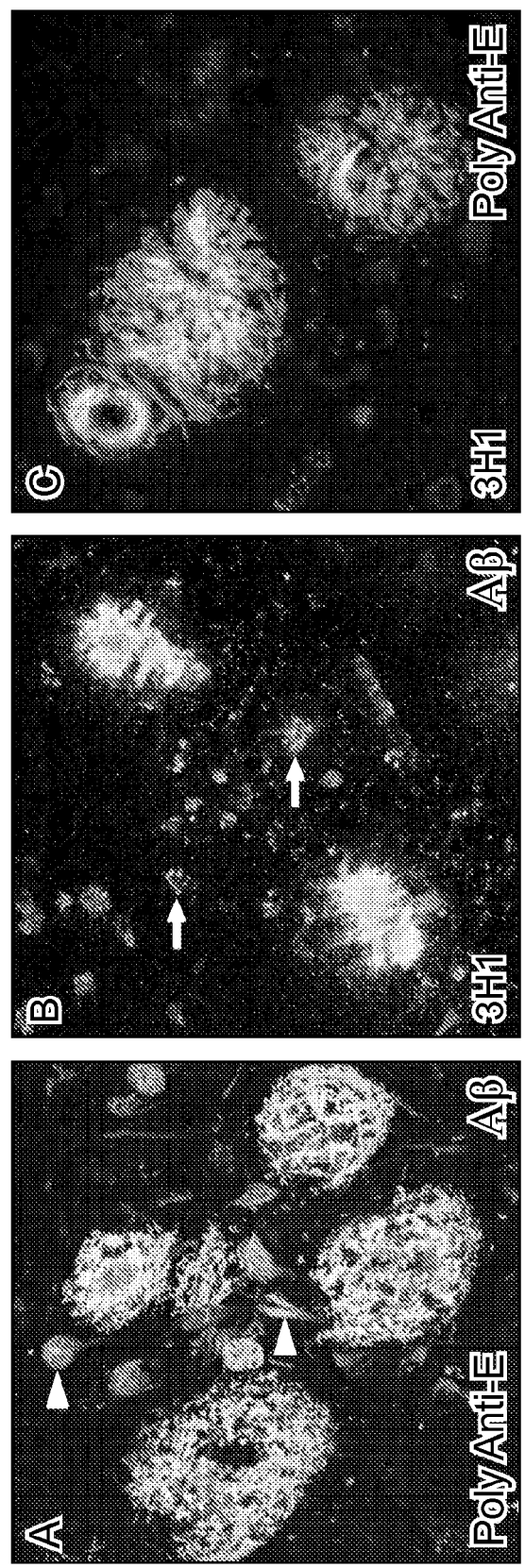
FIGS. 5A-C depict 3H1 recognition of apoE in the center of amyloid plaques in human AD brains.

Double immunofluorescence staining with polyclonal anti-apoE and monoclonal anti-Aβ (3D6) revealed apoE in the center and the edges of amyloid plaques in AD brains (FIG. 5A). Many neurofibrillary tangles were also stained with the polyclonal anti-apoE (FIG. 5A, arrowheads). Interestingly, 3H1-positive apoE was only in the center of plaques, fully colocalizing with Aβ (FIG. 5B). Double immunofluorescence staining with 3H1 and polyclonal anti-apoE confirmed that a subset of apoE in the center of amyloid plaques assumes a unique 3H1-recognizable conformation (FIG. 5C). Since many smaller Aβ deposits were also positive for 3H1 (FIG. 5B, arrows), this unique 3H1-recognizable conformation of apoE may be involved in the initial interaction of apoE and Aβ and in the subsequent nucleation of amyloid plaque formation.

FIGS. 5A-C. 3H1 only recognizes apoE in the center of amyloid plaques in human AD brains Human AD brain sections were co-immunostained with polyclonal anti-apoE (green) and monoclonal anti-Aβ (3 (red) (A), 3H1 (green) and anti-Aβ (3 (red) (B), or 3H1 (green) and polyclonal anti-apoE (red) (C).

3H1 Inhibits the Interaction of apoE with Aβ Peptides

Figure 6:
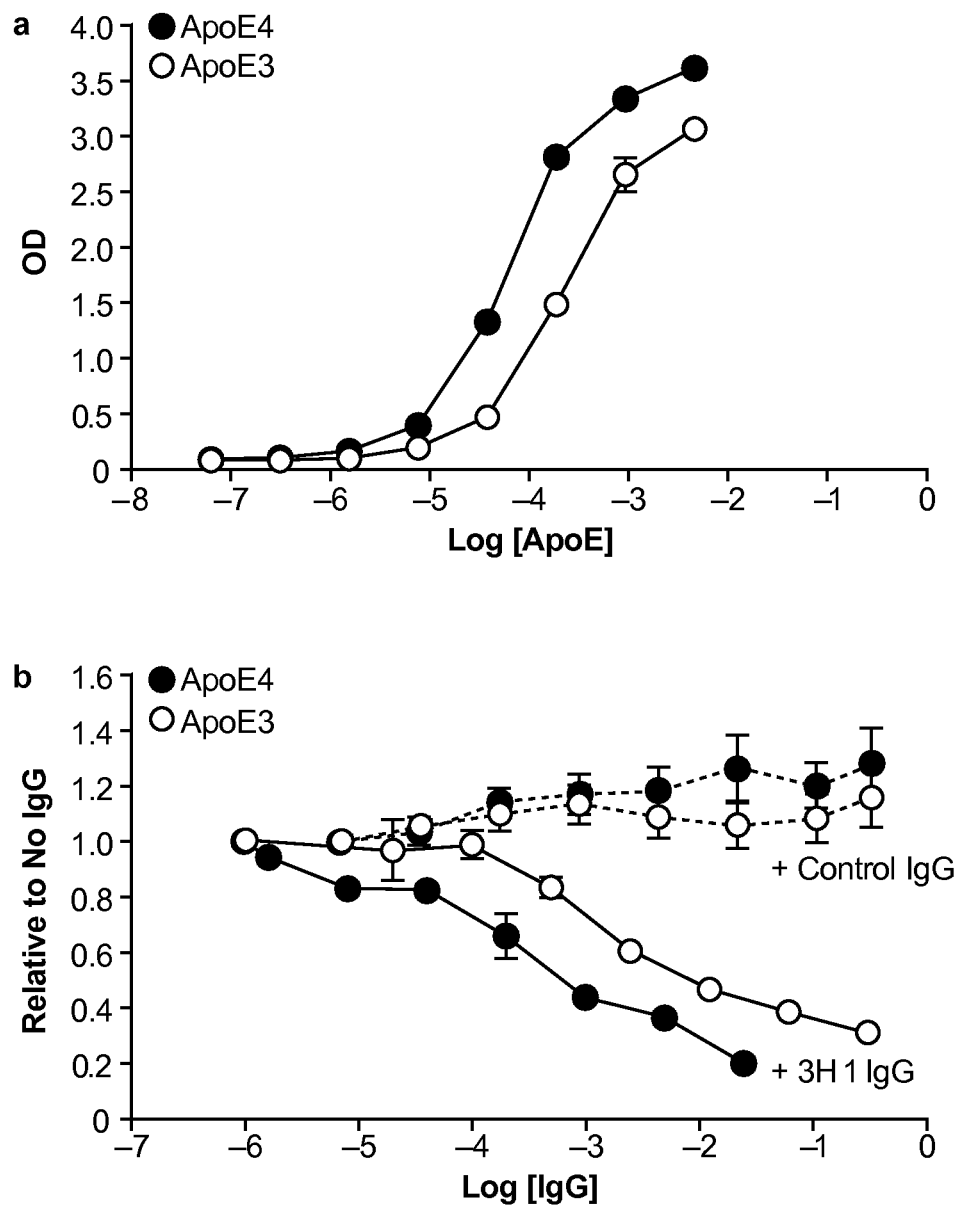
FIGS. 6A and 6B depict 3H1 inhibition of the interaction of apoE with Aβ peptides.
Figure 11:
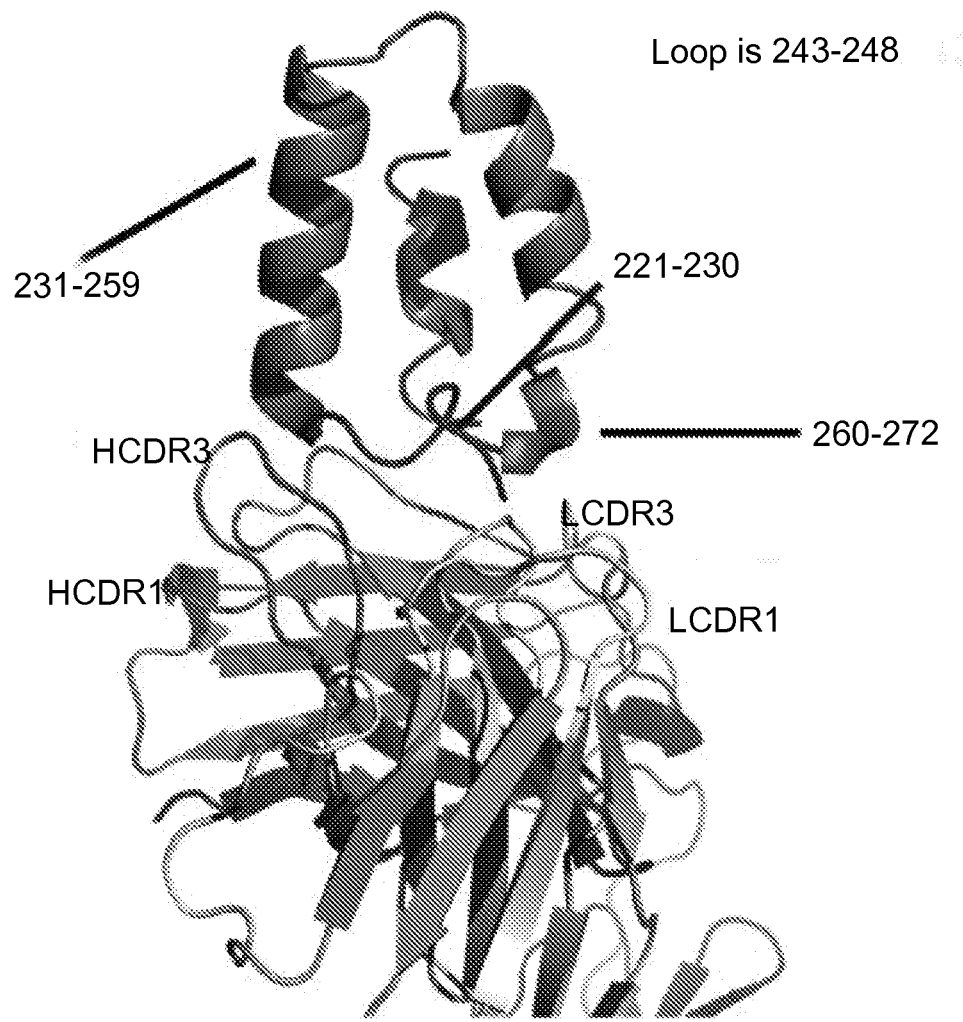
FIGS. 11 and 12 depict 3H1-Fab crystal structure and docking of apoE (221-272).
Figure 12:
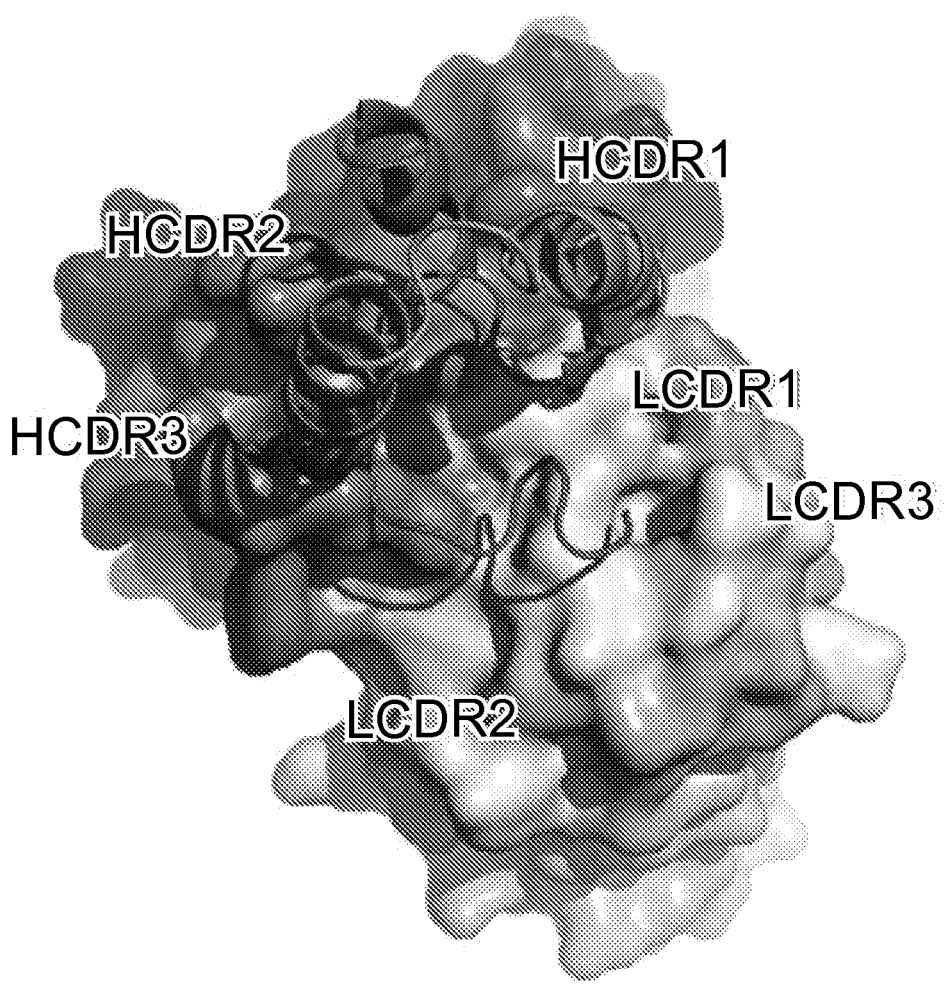

To test whether the 3H1-recognizable conformation of apoE is required for its interaction with Aβ peptides, an ELISA was established in which both apoE3 and apoE4 bound $A\beta_{1-42}$ in a dose-dependent manner. In this assay, apoE4 was more effective than apoE3 in its binding to Aβ (~3-fold) (FIG. 6A), and their binding efficacies matched their reactivity with 3H1 (apoE4>apoE3). Purified 3H1 IgG also inhibited apoE binding to $A\beta_{1-42}$, with a ~90% lower $IC_{50}$ for apoE4 than for apoE3 (FIG. 6B). Binding was not altered by control, nonimmunized mouse IgG (FIG. 6B). Thus, the 3H1-recognizable conformation of apoE determines its binding to $A\beta_{1-42}$.

FIGS. 6A and 6B. 3H1 inhibits the interaction of apoE with Aβ peptides. (A) $A\beta_{1-42}$ was coated onto 96-well microtiter plates (330 ng/well) and allowed to bind to increasing concentrations of recombinant apoE3 or apoE4. After washing, the binding of apoE to Aβ was detected with polyclonal anti-apoE in an ELISA. (B) Increasing amounts of 3H1 IgG or a control mouse IgG were preincubated with apoE3 (28 ng) or apoE4 (9.6 ng) at their $K_d$ (dissociation constant) for Aβ binding. After incubation, the mixture was added to $A\beta_{1-42}$-coated wells, and the binding of apoE to Aβ was detected with polyclonal anti-apoE after washing. All experiments were performed in triplicate. Values are mean±SD. OD, optical density.

REFERENCES

Bales K R, Dodart J C, DeMattos R B, Holtzman D M, Paul S M (2002) Apolipoprotein E, amyloid, and Alzheimer disease. Mol Intery 2:363-375.

Bales K R, Verina T, Cummins D J, Du Y, Dodel R C, Saura J, Fishman C E, DeLong C A, Piccardo P, Petegnief V, Ghetti B, Paul S M (1999) Apolipoprotein E is essential for amyloid deposition in the APP$^{V717F}$ transgenic mouse model of Alzheimer's disease. Proc Natl Acad Sci USA 96:15233-15238.

Bales K R, Verina T, Dodel R C, Du Y, Altstiel L, Bender M, Hyslop P, Johnstone E M, Little S P, Cummins D J, Piccardo P, Ghetti B, Paul S M (1997) Lack of apolipoprotein E dramatically reduces amyloid β-peptide deposition. Nat Genet 17:263-264.

Brecht W J, Harris F M, Chang S, Tesseur I, Yu G-Q, Xu Q, Fish J D, Wyss-Coray T, Buttini M, Mucke L, Mahley R W, Huang Y (2004) Neuron-specific apolipoprotein E4 proteolysis is associated with increased tau phosphorylation in brains of transgenic mice. J Neurosci 24:2527-2534.

Burgess J W, Gould D R, Marcel Y L (1998) The HepG2 extracellular matrix contains separate heparinase- and lipid-releasable pools of apoE. J Biol Chem 273:5645-5654.

Buttini M, Orth M, Bellosta S, Akeefe H, Pitas R E, Wyss-Coray T, Mucke L, Mahley R W (1999) Expression of human apolipoprotein E3 or E4 in the brains of Apoe$^{-/-}$ mice: Isoform-specific effects on neurodegeneration. J Neurosci 19:4867-4880.

Castaño E M, Prelli F, Wisniewski T, Golabek A, Kumar R A, Soto C, Frangione B (1995) Fibrillogenesis in Alzheimer's disease of amyloid β peptides and apolipoprotein E. Biochem J 306:599-604.

Corder E H, Saunders A M, Strittmatter W J, Schmechel D E, Gaskell P C, Small G W, Roses A D, Haines J L, Pericak-Vance M A (1993) Gene dose of apolipoprotein E type 4 allele and the risk of Alzheimer's disease in late onset families. Science 261:921-923.

Du X, Stoops J D, Mertz J R, Stanley C M, Dixon J L (1998) Identification of two regions in apolipoprotein B100 that are exposed on the cytosolic side of the endoplasmic reticulum membrane. J Cell Biol 141:585-599.

Frank P G, Marcel Y L (2000) Apolipoprotein A-I: Structure-function relationships. J Lipid Res 41:853-872.

Gong J-S, Morita S, Kobayashi M, Handa T, Fujita S C, Yanagisawa K, Michikawa M (2007) Novel action of apolipoprotein E (apoE): ApoE isoform specifically inhibits lipid-particle-mediated cholesterol release from neurons. Molec Neurodegeneration 2.

Gong J-S, Kobayashi M, Hayashi H, Zou K, Sawamura N, Fujita S C, Yanagisawa K, Michikawa M (2002) Apolipoprotein E (apoE) isoform-dependent lipid release from astrocytes prepared from human apoE3 and apoE4 knock-in mice. J Biol Chem 277:29919-29926.

Harris F M, Brecht W J, Xu Q, Tesseur I, Kekonius L, Wyss-Coray T, Fish J D, Masliah E, Hopkins P C, Scearce-Levie K, Weisgraber K H, Mucke L, Mahley R W, Huang Y (2003) Carboxyl-terminal-truncated apolipoprotein E4 causes Alzheimer's disease-like neurodegeneration and behavioral deficits in transgenic mice. Proc Natl Acad Sci USA 100:10966-10971.

Hirsch-Reinshagen V, Maia L F, Burgess B L, Blain J-F, Naus K E, Mclsaac S A, Parkinson P F, Chan J Y, Tansley G H, Hayden M R, Poirier J, Van Nostrand W, Wellington C L (2005) The absence of ABCA1 decreases soluble apoE levels but does not diminish amyloid deposition in two murine models of Alzheimer disease. J Biol Chem 280: 43243-43256.

Holtzman D M, Bales K R, Tenkova T, Fagan A M, Parsadanian M, Sartorius L J, Mackey B, Olney J, McKeel D, Wozniak D, Paul S M (2000) Apolipoprotein E isoform-dependent amyloid deposition and neuritic degeneration in a mouse model of Alzheimer's disease. Proc Natl Acad Sci USA 97:2892-2897.

Huang Y (2006a) Molecular and cellular mechanisms of apolipoprotein E4 neurotoxicity and potential therapeutic strategies. Curr Opin Drug Discov Dev 9:627-641.

Huang Y (2006b) Apolipoprotein E and Alzheimer disease. Neurology 66 (Suppl. 1):S79-S85.

Huang Y, Weisgraber K H, Mucke L, Mahley R W (2004) Apolipoprotein E. Diversity of cellular origins, structural and biophysical properties, and effects in Alzheimer's disease. J Mol Neurosci 23:189-204.

Huang Y, Liu X Q, Wyss-Coray T, Brecht W J, Sanan D A, Mahley R W (2001) Apolipoprotein E fragments present in Alzheimer's disease brains induce neurofibrillary tangle-like intracellular inclusions in neurons. Proc Natl Acad Sci USA 98:8838-8843.

Jordan J, Galindo M F, Miller R J, Reardon C A, Getz G S, LaDu M J (1998) Isoform-specific effect of apolipoprotein E on cell survival and β-amyloid-induced toxicity in rat hippocampal pyramidal neuronal cultures. J Neurosci 18:195-204.

Koldamova R, Staufenbiel M, Lefterov I (2005) Lack of ABCA1 considerably decreases brain apoE level and increases amyloid deposition in APP23 mice. J Biol Chem 280:43224-43235.

LaDu M J, Falduto M T, Manelli A M, Reardon C A, Getz G S, Frail D E (1994) Isoform-specific binding of apolipoprotein E to β-amyloid. J Biol Chem 269:23403-23406.

LaDu M J, Pederson T M, Frail D E, Reardon C A, Getz G S, Falduto M T (1995) Purification of apolipoprotein E attenuates isoform-specific binding to β-amyloid. J Biol Chem 270:9039-9042.

Mahley R W (1988) Apolipoprotein E: Cholesterol transport protein with expanding role in cell biology. Science 240: 622-630.

Mahley R W, Huang Y (1999) Apolipoprotein E: From atherosclerosis to Alzheimer's disease and beyond. Curr Opin Lipidol 10:207-217.

Mahley R W, Huang Y, Rall S C, Jr. (1999) Pathogenesis of type III hyperlipoproteinemia (dysbetalipoproteinemia): Questions, quandaries, and paradoxes. J Lipid Res 40:1933-1949.

Mahley R W, Weisgraber K H, Huang Y (2006) Apolipoprotein E4: A causative factor and therapeutic target in neuropathology, including Alzheimer's disease. Proc Natl Acad Sci USA 103:5644-5651.

Pillot T, Goethals M, Najib J, Labeur C, Lins L, Chambaz J, Brasseur R, Vandekerckhove J, Rosseneu M (1999) β-Amyloid peptide interacts specifically with the carboxy-terminal domain of human apolipoprotein E: Relevance to Alzheimer's disease. J Neurochem 72:230-237.

Rall S C, Jr., Weisgraber K H, Mahley R W (1982a) Human apolipoprotein E. The complete amino acid sequence. J Biol Chem 257:4171-4178.

Rall S C, Jr., Weisgraber K H, Innerarity T L, Mahley R W (1982b) Structural basis for receptor binding heterogeneity of apolipoprotein E from type III hyperlipoproteinemic subjects. Proc Natl Acad Sci USA 79:4696-4700.

Sadowski M, Pankiewicz J, Scholtzova H, Ripellino J A, Li Y, Schmidt S D, Mathews P M, Fryer J D, Holtzman D M, Sigurdsson E M, Wisniewski T (2004) A synthetic peptide blocking the apolipoprotein E/β-amyloid binding mitigates β-amyloid toxicity and fibril formation in vitro and reduces β-amyloid plaques in transgenic mice. Am J Pathol 165:937-948.

Sadowski M J, Pankiewicz J, Scholtzova H, Mehta P D, Prelli F, Quartermain D, Wisniewski T (2006) Blocking the apolipoprotein E/amyloid-β interaction as a potential therapeutic approach for Alzheimer's disease. Proc Natl Acad Sci USA 103:18787-18792.

Sanan D A, Weisgraber K H, Russell S J, Mahley R W, Huang D, Saunders A, Schmechel D, Wisniewski T, Frangione B, Roses A D, Strittmatter W J (1994) Apolipoprotein E associates with β amyloid peptide of Alzheimer's disease to form novel monofibrils. Isoform apoE4 associates more efficiently than apoE3. J Clin Invest 94:860-869.

Schmechel D E, Saunders A M, Strittmatter W J, Crain B J, Hulette C M, Joo S H, Pericak-Vance M A, Goldgaber D, Roses A D (1993) Increased amyloid β-peptide deposition in cerebral cortex as a consequence of apolipoprotein E genotype in late-onset Alzheimer disease. Proc Natl Acad Sci USA 90:9649-9653.

Stine W B, Jr, Dahlgren K N, Krafft G A, LaDu M J (2003) In vitro characterization of conditions for amyloid-β peptide oligomerization and fibrillogenesis. J Biol Chem 278: 11612-11622.

Strittmatter W J, Weisgraber K H, Huang D Y, Dong L-M, Salvesen G S, Pericak-Vance M, Schmechel D, Saunders A M, Goldgaber D, Roses A D (1993) Binding of human apolipoprotein E to synthetic amyloid β peptide: Isoform-specific effects and implications for late-onset Alzheimer disease. Proc Natl Acad Sci USA 90:8098-8102.

Tokuda T, Calero M, Matsubara E, Vidal R, Kumar A, Permanne B, Zlokovic B, Smith J D, Ladu M J, Rostagno A, Frangione B, Ghiso J (2000) Lipidation of apolipoprotein E influences its isoform-specific interaction with Alzheimer's amyloid β peptides. Biochem J 348:359-365.

Vedhachalam C, Narayanaswami V, Neto N, Forte T M, Phillips M C, Lund-Katz S, Bielicki J K (2007) The C-terminal lipid-binding domain of apolipoprotein E is a highly efficient mediator of ABCA1-dependent choleserol efflux that promotes the assembly of high-density lipoproteins. Biochemistry 46:2583-2593.

Wahrle S E, Jiang H, Parsadanian M, Hartman R E, Bales K R, Paul S M, Holtzman D M (2005) Deletion of Abca1 increases Aβ deposition in the PDAPP transgenic mouse model of Alzheimer disease. J Biol Chem 280:43236-43242.

Wahrle S E, Jiang H, Parsadanian M, Kim J, Li A, Knoten A, Jain S, Hirsch-Reinshagen V, Wellington C L, Bales K R, Paul S M, Holtzmn D M (2008) Overexpression of ABCA1 reduces amyloid deposition in the PDAPP mouse model of Alzheimer disease. J Clin Invest 118:671-682.

Weisgraber K H (1994) Apolipoprotein E: Structure—function relationships. Adv Protein Chem 45:249-302.

Weisgraber K H, Mahley R W (1996) Human apolipoprotein E: The Alzheimer's disease connection. FASEB J 10:1485-1494.

Weisgraber K H, Rall S C, Jr., Mahley R W (1981) Human E apoprotein heterogeneity. Cysteine-arginine interchanges in the amino acid sequence of the apo-E isoforms. J Biol Chem 256:9077-9083.

Weisgraber K H, Rall S C, Jr., Mahley R W, Milne R W, Marcel Y L, Sparrow J T (1986) Human apolipoprotein E. Determination of the heparin binding sites of apolipoprotein E3. J Biol Chem 261:2068-2076.

Wisniewski T, Castano E M, Golabek A, Vogel T, Frangione B (1994) Acceleration of Alzheimer's fibril formation by apolipoprotein E in vitro. Am J Pathol 145:1030-1035.

Xu Q, Brecht W J, Weisgraber K H, Mahley R W, Huang Y (2004) Apolipoprotein E4 domain interaction occurs in living neuronal cells as determined by fluorescence resonance energy transfer. J Biol Chem 279:25511-25516.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A humanized antibody that specifically binds an epitope in apolipoprotein E (apoE), wherein the epitope comprises amino acid residues within amino acids 222-230 (SEQ ID NO:14) and 261-272 (SEQ ID NO:19) of apoE, wherein the humanized antibody comprises a heavy chain region and a light chain region, wherein the heavy chain region comprises a heavy chain variable region comprising complementarity determining regions (CDRs) having amino acid sequences set forth in SEQ ID NO:2, SEQ ID NO:3, and SEQ ID NO:4, and the light chain region comprises a light chain variable region comprising CDRs having amino acid sequences set forth in SEQ ID NO:6, SEQ ID NO:7, and SEQ ID NO:8.

2. The humanized antibody of claim 1, wherein the light chain variable region is humanized.

3. The humanized antibody of claim 1, wherein the light chain region and the heavy chain region are present in separate polypeptides.

4. The humanized antibody of claim 1, wherein the light chain region and the heavy chain region are present in a single polypeptide.

5. The humanized antibody of claim 1, wherein the antibody binds the epitope with an affinity of from about $10^7$ M$^{-1}$ to about $10^{12}$ M$^{-1}$.

6. The humanized antibody of claim 1, wherein the heavy chain region comprises a constant region, and wherein the constant region is of the isotype IgG1, IgG2, IgG3, or IgG4.

7. The humanized antibody of claim 1, wherein the antibody is detectably labeled.

8. The humanized antibody of claim 1, wherein the antibody is a Fv, scFv, Fab, F(ab')2, or Fab'.

9. The humanized antibody of claim 1, wherein the antibody comprises a covalently linked non-peptide synthetic polymer.

10. The humanized antibody of claim 9, wherein the synthetic polymer is poly(ethylene glycol) polymer.

11. The humanized antibody of claim 1, wherein the antibody comprises a covalently linked lipid or fatty acid moiety.

12. The humanized antibody of claim 1, wherein the antibody comprises a covalently linked polysaccharide or carbohydrate moiety.

13. The humanized antibody of claim 1, wherein the antibody comprises a contrast agent.

14. The humanized antibody of claim 1, wherein the antibody comprises an affinity domain.

15. The humanized antibody of claim 1, wherein the antibody is immobilized on a solid support.

16. The humanized antibody of claim 1, wherein the antibody is a single chain Fv (scFv) antibody.

17. The humanized antibody of claim 16, wherein the scFv is multimerized.

18. The humanized antibody of claim 1, wherein the antibody comprises a polyamine modification.

19. A pharmaceutical composition comprising:
a) the humanized antibody of claim 1; and
b) a pharmaceutically acceptable carrier.

20. The pharmaceutical composition of claim 19, wherein the antibody is encapsulated in a liposome.

* * * * *

SEQUENCE LISTING

```
<160> NUMBER OF SEQ ID NOS: 41

<210> SEQ ID NO 1
<211> LENGTH: 122
<212> TYPE: PRT
<213> ORGANISM: Artificial Sequence
<220> FEATURE:
<223> OTHER INFORMATION: 3H1 heavy chain variable region

<400> SEQUENCE: 1

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Phe Tyr Tyr Gly Gly Ser Tyr Asp Tyr Phe Asp Tyr
            100                 105                 110

Trp Gly Gln Gly Thr Thr Leu Thr Val Ser
        115                 120

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Gly Phe Thr Phe Ser Ser Tyr Ala Met Ser
 1               5                  10

<210> SEQ ID NO 3
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 3

Thr Ile Ser Ser Gly Gly Ser Tyr Thr Tyr Tyr Pro Asp Ser Val Lys
 1               5                  10                  15
```

Gly

```
<210> SEQ ID NO 4
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 4

Gln Phe Tyr Tyr Tyr Gly Gly Ser Tyr Asp Tyr Phe Asp Tyr
 1               5                  10

<210> SEQ ID NO 5
<211> LENGTH: 108
<212> TYPE: PRT
<213> ORGANISM: Artificial Sequence
<220> FEATURE:
<223> OTHER INFORMATION: 3H1 light chain variable region

<400> SEQUENCE: 5

Asp Ile Val Leu Thr Gln Ser Pro Ala Thr Leu Ser Val Thr Pro Gly
 1               5                  10                  15

Asp Ser Val Ser Leu Ala Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Tyr Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Val Gly Thr Lys Leu Glu Ile Lys Arg
            100                 105

<210> SEQ ID NO 6
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 6

Arg Ala Ser Gln Ser Ile Ser Asn Asn Leu His
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Tyr Ala Tyr Gln Ser Ile Ser
 1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide
```

<400> SEQUENCE: 8

Gln Gln Ser Asn Ser Trp Pro Leu Thr
 1               5

<210> SEQ ID NO 9
<211> LENGTH: 366
<212> TYPE: DNA
<213> ORGANISM: Artificial Sequence
<220> FEATURE:
<223> OTHER INFORMATION: 3H1 heavy chain variable region

<400> SEQUENCE: 9

```
gaggtgcagc tggtggagtc tgggggaggc ttagtgaagc ctggagggtc cctgaaactc     60
tcctgtgcag cctctggatt cactttcagt agctatgcca tgtcttgggt tcgccagact    120
ccggagaaga ggctggagtg ggtcgcaacc attagtagtg gtggtagtta cacctactat    180
ccagacagtg tgaaggggcg attcaccatc tccagagaca atgccaagaa caccctgtac    240
ctgcaaatga gcagtctgag gtctgaggac acggccatgt attactgtgc aagacaattt    300
tattactacg gtggtagcta cgactacttt gactactggg gccaagggac cacgctcacc    360
gtctcg                                                                366
```

<210> SEQ ID NO 10
<211> LENGTH: 324
<212> TYPE: DNA
<213> ORGANISM: Artificial Sequence
<220> FEATURE:
<223> OTHER INFORMATION: 3H1 light chain variable region

<400> SEQUENCE: 10

```
gacattgtgc tgacccagtc tccagccacc ctgtctgtga ctccaggaga tagcgtcagt     60
cttgcctgca gggccagcca aagtattagc aacaacctac actggtatca acaaaaatca    120
catgagtctc caaggcttct catcaaatat gcttaccagt ccatctctgg gatcccctcc    180
aggttcagtg gcagtggatc agggacagat ttcactctca gtatcaacag tgtggagact    240
gaagattttg gaatgtattt ctgtcaacag agtaacagct ggcctctcac gttcggtgtg    300
gggaccaagc tggaaataaa acgt                                            324
```

<210> SEQ ID NO 11
<211> LENGTH: 299
<212> TYPE: PRT
<213> ORGANISM: Homo sapiens

<400> SEQUENCE: 11

Lys Val Glu Gln Ala Val Glu Thr Glu Pro Glu Pro Glu Leu Arg Gln
 1               5                  10                  15

Gln Thr Glu Trp Gln Ser Gly Gln Arg Trp Glu Leu Ala Leu Gly Arg
                20                  25                  30

Phe Trp Asp Tyr Leu Arg Trp Val Gln Thr Leu Ser Glu Gln Val Gln
            35                  40                  45

Glu Glu Leu Leu Ser Ser Gln Val Thr Gln Glu Leu Arg Ala Leu Met
        50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Arg

```
            100                 105                 110
Gly Arg Leu Val Gln Tyr Arg Gly Glu Val Gln Ala Met Leu Gly Gln
            115                 120                 125

Ser Thr Glu Glu Leu Arg Val Arg Leu Ala Ser His Leu Arg Lys Leu
        130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295

<210> SEQ ID NO 12
<211> LENGTH: 317
<212> TYPE: PRT
<213> ORGANISM: Homo sapiens

<400> SEQUENCE: 12

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175
```

```
Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 13
<211> LENGTH: 43
<212> TYPE: PRT
<213> ORGANISM: Homo sapiens

<400> SEQUENCE: 13

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 14
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 14

Gly Ser Arg Thr Arg Asp Arg Leu Asp
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 15

Lys Ser Trp Phe Glu Pro Leu Val Glu Asp Met
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 16
```

```
Ser Arg Thr Arg Asp Arg Leu
 1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Ser Trp Phe Glu Pro Leu Val Glu Asp
 1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 18

Gly Ser Arg Thr Arg Asp Arg Leu Asp Glu Val
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 19

Leu Lys Ser Trp Phe Glu Pro Leu Val Glu Asp Met
 1               5                  10

<210> SEQ ID NO 20
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 20

Lys Glu Gln Val Ala Glu Val Arg Ala Lys Leu Glu Glu Gln Ala Gln
 1               5                  10                  15

Gln Ile Arg Leu Gln Ala Glu Ala Phe Gln Ala Arg
                20                  25

<210> SEQ ID NO 21
<211> LENGTH: 51
<212> TYPE: PRT
<213> ORGANISM: Artificial Sequence
<220> FEATURE:
<223> OTHER INFORMATION: Synthetic polypeptide

<400> SEQUENCE: 21

Gly Ser Arg Thr Arg Asp Arg Leu Asp Glu Val Lys Glu Gln Val Ala
 1               5                  10                  15

Glu Val Arg Ala Lys Leu Glu Glu Gln Ala Gln Gln Ile Arg Leu Gln
                20                  25                  30

Ala Glu Ala Phe Gln Ala Arg Leu Lys Ser Trp Phe Glu Pro Leu Val
            35                  40                  45

Glu Asp Met
```

50

```
<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 22

Gly Ser Gly Gly Ser
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 23

Gly Gly Gly Ser
1

<210> SEQ ID NO 24
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 24

Gly Gly Ser Gly
1

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 25

Gly Gly Ser Gly Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 26

Gly Ser Gly Ser Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 27

Gly Ser Gly Gly Gly
1               5
```

```
<210> SEQ ID NO 28
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 28

Gly Gly Gly Ser Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 29

Gly Ser Ser Ser Gly
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 30

Cys Tyr Pro Tyr Asp Val Pro Asp Tyr Ala
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 31

Asp Tyr Lys Asp Asp Asp Asp Lys
1               5

<210> SEQ ID NO 32
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 32

Cys Glu Gln Lys Leu Ile Ser Glu Glu Asp Leu
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 33

His His His His His
1               5
```

```
<210> SEQ ID NO 34
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 34

His His His His His His
 1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 35

Glu Gln Lys Leu Ile Ser Glu Glu Asp Leu
 1               5                  10

<210> SEQ ID NO 36
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 36

Asp Tyr Lys Asp Asp Asp Asp Lys
 1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 37

Trp Ser His Pro Gln Phe Glu Lys
 1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 38

Tyr Pro Tyr Asp Val Pro Asp Tyr Ala
 1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 39

Arg Tyr Ile Arg Ser
 1               5
```

```
<210> SEQ ID NO 40
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 40

Phe His His Thr
 1

<210> SEQ ID NO 41
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 41

Trp Glu Ala Ala Ala Arg Glu Ala Cys Cys Arg Glu Cys Cys Ala Arg
 1               5                  10                  15

Ala
```